(12) United States Patent
Adamer et al.

(10) Patent No.: US 11,970,450 B2
(45) Date of Patent: Apr. 30, 2024

(54) MULTI-COMPONENT CRYSTALS OF AN ORALLY AVAILABLE HIF PROLYL HYDROXYLASE INHIBITOR

(71) Applicant: Sandoz AG, Basel (CH)

(72) Inventors: Verena Adamer, Kundl (AT); Andrea Thaler, Kundl (AT); Erwin Schreiner, Kundl (AT)

(73) Assignee: Sandoz AG, Basel (CH)

( * ) Notice: Subject to any disclaimer, the term of this patent is extended or adjusted under 35 U.S.C. 154(b) by 428 days.

(21) Appl. No.: 17/297,790

(22) PCT Filed: Nov. 7, 2019

(86) PCT No.: PCT/EP2019/080511
§ 371 (c)(1),
(2) Date: May 27, 2021

(87) PCT Pub. No.: WO2020/108941
PCT Pub. Date: Jun. 4, 2020

(65) Prior Publication Data
US 2022/0024874 A1  Jan. 27, 2022

(30) Foreign Application Priority Data

Nov. 28, 2018  (EP) .................................. 18208845

(51) Int. Cl.
*C07D 213/81* (2006.01)
*C07D 207/16* (2006.01)
(52) U.S. Cl.
CPC ......... *C07D 213/81* (2013.01); *C07D 207/16* (2013.01); *C07B 2200/13* (2013.01)
(58) Field of Classification Search
CPC .. C07D 213/81; C07D 207/16; C07B 2200/13
See application file for complete search history.

(56) References Cited

U.S. PATENT DOCUMENTS

2020/0095203 A1   3/2020  Chen et al.

FOREIGN PATENT DOCUMENTS

| WO | 2008/002576 | * | 1/2008 |
| WO | 2008002576 A2 | | 1/2008 |
| WO | 2012170377 A1 | | 12/2012 |
| WO | 2015073779 A1 | | 5/2015 |
| WO | 2018/108101 | * | 6/2018 |
| WO | 2018108101 A1 | | 6/2018 |

OTHER PUBLICATIONS

Liu, E J Parm and Biopharm, 2016, 107, 151-159. (Year: 2016).*
Chertow, New England J of Med, Apr. 2021, 384(17), 1589-1600. (Year: 2021).*
Liu, Mingyu, et al., European Journal of Pharmaceutics and Biopharmaceutics, vol. 107, Oct. 2016, pp. 151-159.
Pecharsky, et al., Fundamentals of powder diffraction and structural characterization of materials, 2005, Springer, p. 3.
International Search Report and Written Opinion for PCT/EP2019/080511, dated Jun. 4, 2020, 10 pages.

* cited by examiner

*Primary Examiner* — D Margaret M Seaman
(74) *Attorney, Agent, or Firm* — Luedeka Neely, P.C.

(57) ABSTRACT

The present invention relates to crystalline compounds comprising vadadustat and L-proline and processes for their preparation. Furthermore, the invention relates to a pharmaceutical composition comprising one or more of the crystalline compounds of the present invention and at least one pharmaceutically acceptable excipient. The pharmaceutical composition of the present invention can be used as a medicament, in particular for the treatment and/or prevention of anemia for example in patients with end-stage renal disease (ESRD) and/or chronic kidney disease (CKD).

17 Claims, 12 Drawing Sheets

MULTI-COMPONENT CRYSTALS OF AN ORALLY AVAILABLE HIF PROLYL HYDROXYLASE INHIBITOR

This application is a Section 371 national phase entry of PCT application PCT/EP2019/080511, filed Nov. 7, 2019. This application also claims the benefit of the earlier filing date of European patent application 18208845.0, filed Nov. 28, 2018.

FIELD OF THE INVENTION

The present invention relates to crystalline compounds comprising vadadustat and L-proline and processes for their preparation. Furthermore, the invention relates to a pharmaceutical composition comprising one or more of the crystalline compounds of the present invention and at least one pharmaceutically acceptable excipient. The pharmaceutical composition of the present invention can be used as a medicament, in particular for the treatment and/or prevention of anemia for example in patients with end-stage renal disease (ESRD) and/or chronic kidney disease (CKD).

BACKGROUND OF THE INVENTION

Vadadustat is an experimental orally available hypoxia inducible factor prolyl hydroxylase inhibitor (HIF-PHI). HIF-PHIs are a new class of small molecules under clinical development for anemia correction. They share a common mechanism of action, i.e. the stabilization of the hypoxia-inducible transcription factors, the main mediators of the effects of hypoxia on the body and thus are useful for treating and preventing HIF associated disorders including anemia-, ischemia- and hypoxia-related disorders.

Vadadustat may chemically be designated as 2-[[5-(3-chlorophenyl)-3-hydroxypyridine-2-carbonyl)amino]acetic acid or {[5-(3-chlorophenyl)-3-hydroxypyridine-2-carbonyl]amino}acetic acid and can be represented by the chemical structure as depicted in Formula (I):

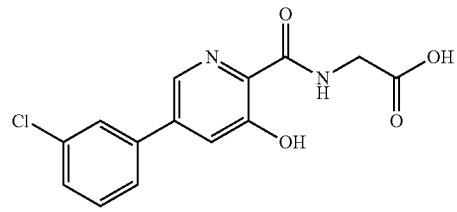

Formula (I)

The compound vadadustat is obtained as colorless solid in Example 2 of WO 2008/002576 A2. In Examples 3 and 4 of WO 2012/170377 A1 vadadustat is obtained as white solid. WO 2015/073779 A1 discloses single-component crystal forms of vadadustat designated as Form A, Form B and Form C, respectively. Further single-component crystal forms of vadadustat are Form CS1 and CS8 disclosed in WO 2018/108101 A1. An amorphous form of vadadustat is disclosed in IPCOM000254772D. The only multiple-component crystal form of vadadustat described so far is the hydrate denominated CS2 of WO 2018/108101 A1.

However, hydrate CS2 of WO 2018/108101 A1 suffers from certain drawbacks e.g. it is physically unstable upon temperature stress and readily loses its water leading to phase transformation. This is critical, because the sudden appearance or disappearance of a solid-state form of an active pharmaceutical ingredient can pose a problem in process development. Similarly, serious pharmaceutical consequences can arise if transformation occurs in a dosage form.

It is thus an objective of the present invention to provide an improved solid-state form of vadadustat which is physically stable against temperature stress

SUMMARY OF THE INVENTION

The present invention solves the above mentioned problem by providing crystalline compounds comprising vadadustat and L-proline. The crystalline compounds of the present invention may be present as co-crystals, salts or mixtures thereof. Most preferably, the crystalline compounds of the present invention are co-crystals.

Apart from conventional solid-state forms of an API, such as polymorphs and pseudopolymorphs (hydrates and solvates), pharmaceutical co-crystals open up further opportunities for customizing the physicochemical properties of APIs with a process or clinical need. For example, they can be tailored to enhance drug product bioavailability and stability and to enhance the processability of APIs during drug product manufacture. Thereby, co-crystals are structurally related to hydrates and solvates, since they contain more than one component in the crystal lattice and the interaction between these components is due to nonionic forces.

The crystalline compounds of the present invention comprising vadadustat and L-proline possess one or more improved physicochemical properties selected from dissolution rate, solubility, chemical stability, physical stability, hygroscopicity, melting point, morphology, flowability, bulk density and compressibility. In particular, they are thermally more stable compared to the hydrate CS2 of WO 2018/108101 A1 and also compared to the 1,4-dioxane solvate described hereinafter and preserve their crystal structure when exposed to temperature stress.

Abbreviations

PXRD powder X-ray diffractogram
FTIR Fourier transform infrared
ATR attenuated total reflection
DSC differential scanning calorimetry
TGA thermogravimetric analysis
GC gas chromatography
MS mass spectrometry
RT room temperature

Definitions

As used herein the term "room temperature" refers to a temperature in the range of from 20 to 30° C.

The term "co-crystal" as used herein refers to a crystalline material composed of two or more different molecular and/or ionic compounds in the same crystal lattice, wherein the different compounds interact via nonionic and noncovalent forces, and at least two of the individual molecular and/or ionic compounds are solids at room temperature.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C. Typically, standard conditions can additionally mean a measurement under 20-50% relative humidity.

The term "reflection" with regard to powder X-ray diffraction as used herein, means peaks in an X-ray diffractogram, which are caused at certain diffraction angles (Bragg angles) by constructive interference from X-rays scattered by parallel planes of atoms in solid material, which are distributed in an ordered and repetitive pattern in a long-range positional order. Such a solid material is classified as crystalline material, whereas amorphous material is defined as solid material, which lacks long-range order and only displays short-range order, thus resulting in broad scattering. According to literature, long-range order e.g. extends over approximately 100 to 1000 atoms, whereas short-range order is over a few atoms only (see "*Fundamentals of Powder Diffraction and Structural Characterization of Materials*" by Vitalij K Pecharsky and Peter Y. Zavalij, Kluwer Academic Publishers, 2003, page 3).

The term "essentially the same" with reference to powder X-ray diffraction means that variabilities in reflection positions and relative intensities of the reflections are to be taken into account. For example, a typical precision of the 2-Theta values is in the range of ±0.2° 2-Theta, preferably in the range of ±0.1° 2-Theta. Thus, a reflection that usually appears at 8.2° 2-Theta for example can appear between 8.0° and 8.4° 2-Theta, preferably between 8.1 and 8.3° 2-Theta on most X-ray diffractometers under standard conditions. Furthermore, one skilled in the art will appreciate that relative reflection intensities will show inter-apparatus variability as well as variability due to degree of crystallinity, preferred orientation, sample preparation and other factors known to those skilled in the art and should be taken as qualitative measure only.

The term "essentially the same" with reference to Fourier transform infrared spectroscopy means that variabilities in peak positions and relative intensities of the peaks are to be taken into account. For example, a typical precision of the wavenumber values is in the range of ±4 $cm^{-1}$, preferably of ±2 $cm^{-1}$. Thus, a peak at 3383 $cm^{-1}$ for example can appear in the range of from 3379 to 3387 $cm^{-1}$, preferably of from 3381 to 3385 $cm^{-1}$ on most infrared spectrometers under standard conditions. Differences in relative intensities are typically smaller compared to X-ray diffraction. However, one skilled in the art will appreciate that small differences in peak intensities due to degree of crystallinity, sample preparation and other factors can also occur in infrared spectroscopy. Relative peak intensities should therefore be taken as qualitative measure only.

The term "solid-state form" as used herein refers to any crystalline and/or amorphous phase of a compound. Crystalline phases include anhydrous/non-solvated forms of a compound and their polymorphs, hydrates and solvates of a compound and their polymorphs, salts and co-crystals of a compound and any mixtures thereof.

The terms "anhydrous" or "anhydrate" as used herein refer to a crystalline solid where no water is cooperated in or accommodated by the crystal structure. Anhydrous forms may still contain residual water, which is not part of the crystal structure but may be adsorbed on the surface or absorbed in disordered regions of the crystal.

The term "non-solvated" as used herein refers to a crystalline solid where no organic solvent is cooperated in or accommodated by the crystal structure. Non-solvated forms may still contain residual organic solvents, which are not part of the crystal structure but may be adsorbed on the surface or absorbed in disordered regions of the crystal.

The crystalline compounds comprising vadadustat and L-proline of the present invention may be referred to herein as being characterized by a powder X-ray diffractogram and/or a Fourier transform infrared spectrum "as shown in" a figure. The person skilled in the art understands that factors such as variations in instrument type, response and variations in sample directionality, sample concentration, sample purity, sample history and sample preparation may lead to variations, for example relating to the exact reflection or peak positions and intensities. However, a comparison of the graphical data in the figures herein with the graphical data generated for an unknown physical form and the confirmation that two sets of graphical data relate to the same crystal form is well within the knowledge of a person skilled in the art.

As used herein, the term "mother liquor" refers to the solution remaining after crystallization of a solid from said solution.

A "predetermined amount" as used herein with regard to crystalline vadadustat L-proline of the present invention refers to the initial amount of the crystalline vadadustat L-proline used for the preparation of a pharmaceutical composition having a desired dosage strength of vadadustat.

As used herein, the term "effective amount" in conjunction with crystalline vadadustat L-proline of the present invention encompasses an amount of crystalline vadadustat L-proline which causes the desired therapeutic or prophylactic effect.

As used herein, the term "about" means within a statistically meaningful range of a value. Such a range can be within an order of magnitude, typically within 10%, more typically within 5%, even more typically within 1% and most typically within 0.1% of the indicated value or range. Sometimes, such a range can lie within the experimental error, typical of standard methods used for the measurement and/or determination of a given value or range.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The term "diluent" as used herein refers to substances that are used to dilute the active pharmaceutical ingredient prior to delivery. Diluents can also serve as stabilizers.

The terms "disintegrant" or "disintegrating agent" as used herein refers to substances which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances which are added to a powder blend to prevent the compacted powder mass from sticking to the equipment during tableting or encapsulation process. They aid the ejection of the tablet from the dies and can improve powder flow.

The term "glidant" as used herein refers to substances which are used for tablet and capsule formulations in order to improve flow properties during tablet compression and to produce an anti-caking effect.

DETAILED DESCRIPTION OF THE INVENTION

Figure 1:
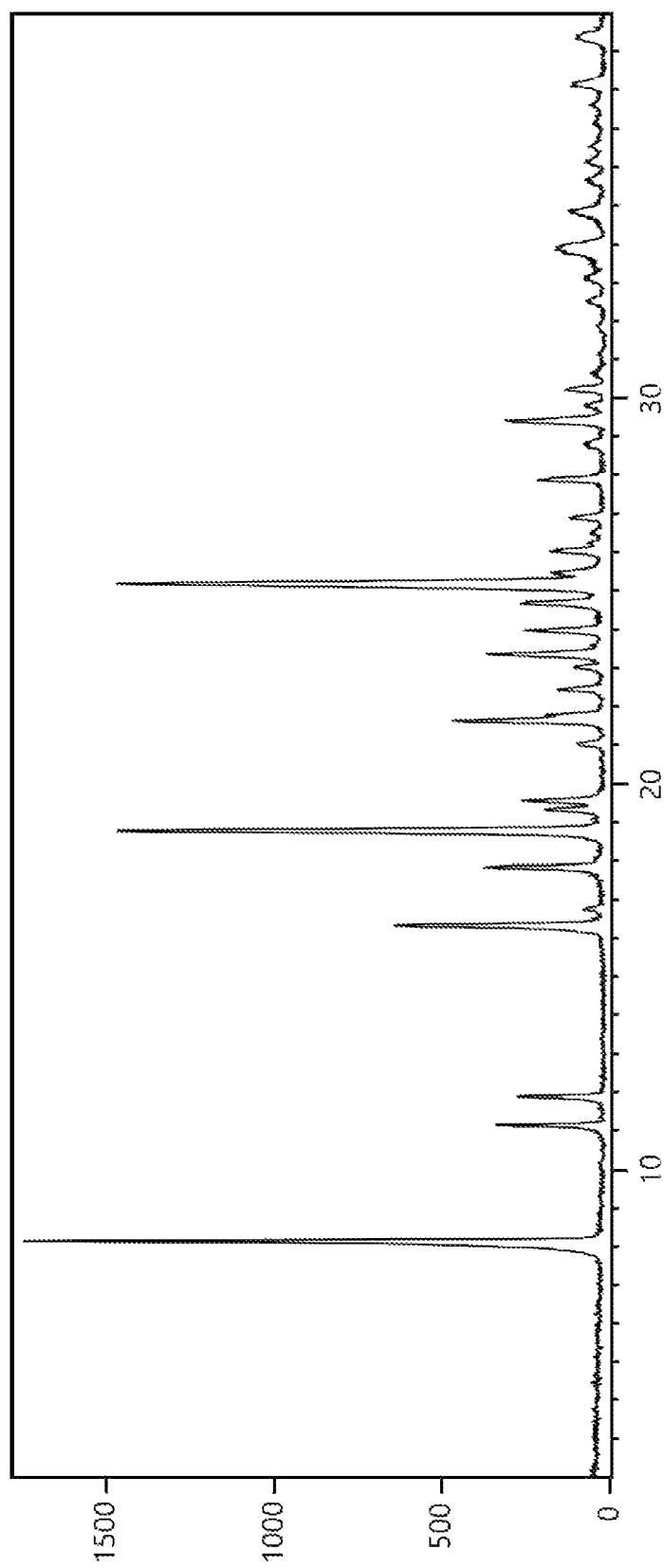
FIG. 1: illustrates a representative PXRD of vadadustat L-proline Form 1 according to the present invention. The x-axis shows the scattering angle in ° 2-Theta, the y-axis shows the intensity of the scattered X-ray beam in counts of detected photons.

The present invention relates to crystalline compounds comprising vadadustat and L-proline. The crystalline compounds comprising vadadustat and L-proline of the present invention may be characterized by the chemical structure according to Formula (II)

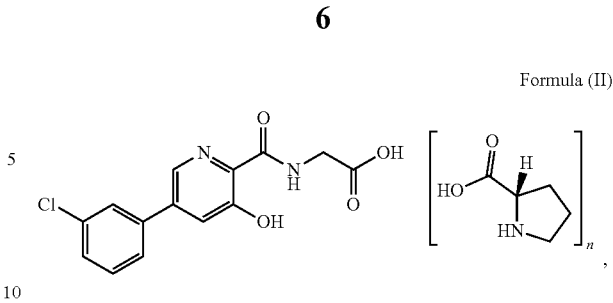

Formula (II)

wherein n is in the range of from 0.7 to 1.7, preferably of from 0.8 to 1.6, more preferably of from 0.9 to 1.5, even more preferably of from 1.0 to 1.4. For example, n is selected from the group consisting of about 0.7, 0.8, 0.9, 1.0, 1.1, 1.2, 1.3, 1.4, 1.5, 1.6 and 1.7. Most preferably, n is 1.0 or 1.4.

Preferably, the crystalline compounds comprising vadadustat and L-proline of the present invention are co-crystals, salts or any mixtures thereof. Most preferably, the crystalline compounds comprising vadadustat and L-proline of the present invention are co-crystals.

In particular, the present invention relates to crystalline compounds comprising vadadustat and L-proline of the present invention, hereinafter also designated as "Form 1" and "Form 2".

Form 1 and Form 2 of vadadustat L-proline of the present invention may be characterized by analytical methods well known in the field of the pharmaceutical industry for characterizing crystalline solids. Such methods comprise but are not limited to powder X-ray diffraction, FTIR spectroscopy, DSC and TGA. Form 1 and Form 2 of vadadustat L-proline of the present invention may be characterized by one of the aforementioned analytical methods or by combining two or more of them. In particular, they may be characterized by any one of the following embodiments or by combining two or more of the following embodiments.

Vadadustat L-Proline Form 1

In one embodiment the invention relates to a crystalline form (Form 1) of vadadustat L-proline, characterized by having a PXRD comprising reflections at 2-Theta angles of:
 (8.2±0.2)°, (18.8±0.2)° and (25.2±0.2)°; or
 (8.2±0.2)°, (16.4±0.2)°, (18.8±0.2)° and (25.2±0.2)°; or
 (8.2±0.2)°, (11.2±0.2)°, (16.4±0.2)°, (18.8±0.2)° and (25.2±0.2)°; or
 (8.2±0.2)°, (11.2±0.2)°, (11.9±0.2)°, (16.4±0.2)°, (18.8±0.2)° and (25.2±0.2)°; or
 (8.2±0.2)°, (11.2±0.2)°, (11.9±0.2)°, (16.4±0.2)°, (17.9±0.2)°, (18.8±0.2)° and (25.2±0.2)°; or
 (8.2±0.2)°, (11.2±0.2)°, (11.9±0.2)°, (16.4±0.2)°, (17.9±0.2)°, (18.8±0.2)°, (21.6±0.2)° and (25.2±0.2)°; or
 (8.2±0.2)°, (11.2±0.2)°, (11.9±0.2)°, (16.4±0.2)°, (17.9±0.2)°, (18.8±0.2)°, (21.6±0.2)°, (23.4±0.2)° and (25.2±0.2)°; or
 (8.2±0.2)°, (11.2±0.2)°, (11.9±0.2)°, (16.4±0.2)°, (17.9±0.2)°, (18.8±0.2)°, (19.6±0.2)°, (21.6±0.2)°, (23.4±0.2)° and (25.2±0.2)°,
when measured at RT with Cu-Kalpha$_{1,2}$ radiation having a wavelength of 0.15419 nm.

Alternatively, the invention relates to a crystalline form (Form 1) of vadadustat L-, characterized by having a PXRD comprising reflections at 2-Theta angles of:
 (8.2±0.1)°, (18.8±0.0)° and (25.2±0.1)°; or
 (8.2±0.1)°, (16.4±0.1)°, (18.8±0.1)° and (25.2±0.1)°; or
 (8.2±0.1)°, (11.2±0.1)°, (16.4±0.1)°, (18.8±0.1)° and (25.2±0.1)°; or (8.2±0.1)°, (11.2±0.1)°, (11.9±0.1)°, (16.4±0.1)°, (18.8±0.1)° and (25.2±0.1)°; or
(8.2±0.1)°, (11.2±0.1)°, (11.9±0.1)°, (16.4±0.1)°, (17.9±0.1)°, (18.8±0.1)° and (25.2±0.1)°; or
(8.2±0.1)°, (11.2±0.1)°, (11.9±0.1)°, (16.4±0.1)°, (17.9±0.1)°, (18.8±0.1)°, (21.6±0.1)° and (25.2±0.1)°; or
(8.2±0.1)°, (11.2±0.1)°, (11.9±0.1)°, (16.4±0.1)°, (17.9±0.1)°, (18.8±0.1)°, (21.6±0.1)°, (23.4±0.1)° and (25.2±0.1)°; or
(8.2±0.1)°, (11.2±0.1)°, (11.9±0.1)°, (16.4±0.1)°, (17.9±0.1)°, (18.8±0.1)°, (19.6±0.1)°, (21.6±0.1)°, (23.4±0.1)° and (25.2±0.1)°,
when measured at a temperature in the range of from 20 to 30° C. with Cu-Kalpha$_{1,2}$ radiation having a wavelength of 0.15419 nm.

Also, the invention relates to a crystalline form (Form 1) of vadadustat L-proline, characterized by having a PXRD essentially the same as shown in FIG. 1 of the present invention, when measured at RT with Cu-Kalpha$_{1,2}$ radiation having a wavelength of 0.15419 nm.

In addition, the present invention relates to a crystalline form (Form 1) of vadadustat L-proline, characterized by having an FTIR spectrum comprising peaks at wavenumbers of:
(3378±4) cm$^{-1}$, (3217±4) cm$^{-1}$ and (1651±4) cm$^{-1}$ or;
(3378±4) cm$^{-1}$, (3217±4) cm$^{-1}$, (1651±4) cm$^{-1}$ and (1532±4) cm$^{-1}$; or
(3378±4) cm$^{-1}$, (3217±4) cm$^{-1}$, (1651±4) cm$^{-1}$, (1532±4) cm$^{-1}$ and (1380±4) cm$^{-1}$; or
(3378±4) cm$^{-1}$, (3217±4) cm$^{-1}$, (1718±4) cm$^{-1}$, (1651±4) cm$^{-1}$, (1532±4) cm$^{-1}$ and (1380±4) cm$^{-1}$; or
(3378±4) cm$^{-1}$, (3217±4) cm$^{-1}$, (1718±4) cm$^{-1}$, (1651±4) cm$^{-1}$, (1532±4) cm$^{-1}$, (1380±4) cm$^{-1}$ and (1772±4) cm$^{-1}$; or
(3378±4) cm$^{-1}$, (3217±4) cm$^{-1}$, (1718±4) cm$^{-1}$, (1651±4) cm$^{-1}$, (1532±4) cm$^{-1}$, (1380±4) cm$^{-1}$, (1314±4) cm$^{-1}$ and (1172±4) cm$^{-1}$; or
(3378±4) cm$^{-1}$, (3217±4) cm$^{-1}$, (1718±4) cm$^{-1}$, (1651±4) cm$^{-1}$, (1532±4) cm$^{-1}$, (1380±4) cm$^{-1}$, (1314±4) cm$^{-1}$, (1172±4) cm$^{-1}$ and (926±4) cm$^{-1}$; or
(3378±4) cm$^{-1}$, (3217±4) cm$^{-1}$, (2985±4) cm$^{-1}$, (1718±4) cm$^{-1}$, (1651±4) cm$^{-1}$, (1532±4) cm$^{-1}$, (1380±4) cm$^{-1}$, (1314±4) cm$^{-1}$, (1172±4) cm$^{-1}$ and (926±4) cm$^{-1}$,
when measured at RT with a diamond ATR cell.

Alternatively, the present invention relates to a crystalline form (Form 1) of vadadustat L-proline, characterized by having an FTIR spectrum comprising peaks at wavenumbers of:
(3378±2) cm$^{-1}$, (3217±2) cm$^{-1}$ and (1651±2) cm$^{-1}$ or;
(3378±2) cm$^{-1}$, (3217±2) cm$^{-1}$, (1651±2) cm$^{-1}$ and (1532±2) cm$^{-1}$; or
(3378±2) cm$^{-1}$, (3217±2) cm$^{-1}$, (1651±2) cm$^{-1}$, (1532±2) cm$^{-1}$ and (1380±2) cm$^{-1}$; or
(3378±2) cm$^{-1}$, (3217±2) cm$^{-1}$, (1718±2) cm$^{-1}$, (1651±2) cm$^{-1}$, (1532±2) cm$^{-1}$ and (1380±2) cm$^{-1}$; or
(3378±2) cm$^{-1}$, (3217±2) cm$^{-1}$, (1718±2) cm$^{-1}$, (1651±2) cm$^{-1}$, (1532±2) cm$^{-1}$, (1380±2) cm$^{-1}$ and (1772±2) cm$^{-1}$; or
(3378±2) cm$^{-1}$, (3217±2) cm$^{-1}$, (1718±2) cm$^{-1}$, (1651±2) cm$^{-1}$, (1532±2) cm$^{-1}$, (1380±2) cm$^{-1}$, (1314±2) cm$^{-1}$ and (1172±2) cm$^{-1}$; or
(3378±2) cm$^{-1}$, (3217±2) cm$^{-1}$, (1718±2) cm$^{-1}$, (1651±2) cm$^{-1}$, (1532±2) cm$^{-1}$, (1380±2) cm$^{-1}$, (1314±2) cm$^{-1}$, (1172±2) cm$^{-1}$ and (926±2) cm$^{-1}$; or
(3378±2) cm$^{-1}$, (3217±2) cm$^{-1}$, (2985±2) cm$^{-1}$, (1718±2) cm$^{-1}$, (1651±2) cm$^{-1}$, (1532±2) cm$^{-1}$, (1380±2) cm$^{-1}$, (1314±2) cm$^{-1}$, (1172±2) cm$^{-1}$ and (926±2) cm$^{-1}$,
when measured at RT with a diamond ATR cell.

Figure 2:
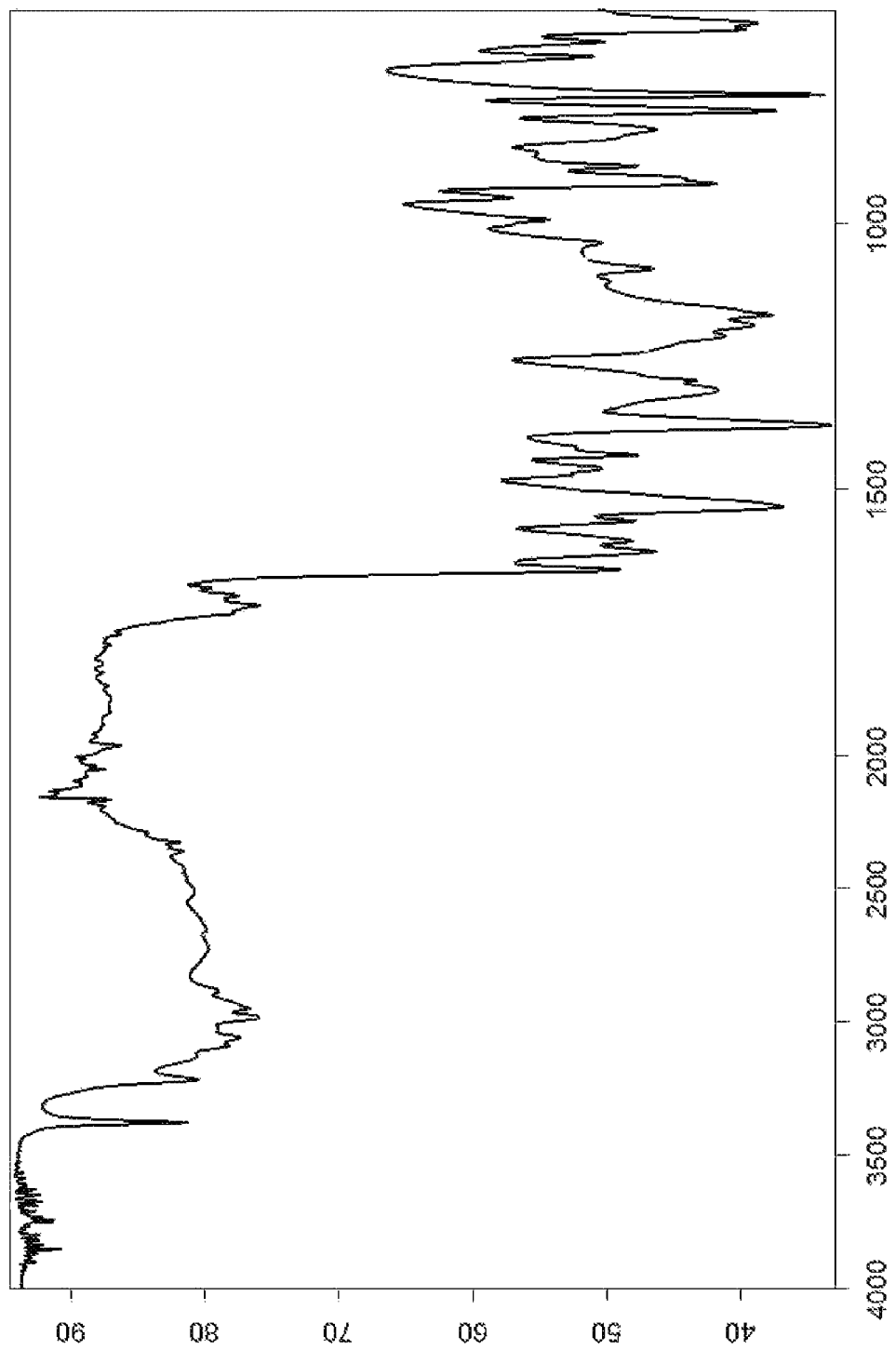
FIG. 2: illustrates a representative FTIR spectrum of vadadustat L-proline Form 1 according to the present invention. The x-axis shows the wavenumbers in $cm^{-1}$, the y-axis shows the relative intensity in percent transmittance.

Moreover, the present invention relates to a crystalline form (Form 1) of vadadustat L-proline, characterized by having an FTIR spectrum essentially the same as shown in FIG. 2 of the present invention, when measured at RT with a diamond ATR cell.

Furthermore, the present invention relates to a crystalline form (Form 1) of vadadustat L-proline, characterized by having a DSC curve comprising an endothermic peak, preferably a single endothermic peak, having an onset at a temperature in the range of from (170±5)° C., preferably of from (170±3)° C., more preferably of from (170±2)° C., even more preferably of from (170±1)° C., for example having an onset at a temperature of about 170° C., when measured with DSC at a heating rate of 10 K/min.

Alternatively, the present invention relates to a crystalline form (Form 1) of vadadustat L-proline, characterized by having a DSC curve comprising an endothermic peak, preferably a single endothermic peak, having a peak maximum at a temperature in the range of from (172±5)° C., preferably of from (172±3)° C., more preferably of from (172±2)° C., even more preferably of from (172±1)° C., for example having a peak maximum at a temperature of about 172° C., when measured with DSC at a heating rate of 10 K/min.

In addition, the invention relates to a crystalline form (Form 1) of vadadustat L-proline, characterized by having a melting point onset at a temperature in the range of from (170±5) ° C., preferably of from (170±3)° C., more preferably of from (170±2)° C., even more preferably of from (170±1)° C., for example having a melting point onset at a temperature of about 170° C., when measured with DSC at a heating rate of 10 K/min.

Furthermore, the present invention relates to a crystalline form (Form 1) of vadadustat L-proline, characterized by having a TGA curve showing a mass loss of not more than 0.5 weight %, preferably of not more than 0.2 weight % based on the weight of the crystalline form, when heated from 25 to 170° C. at a rate of 10 K/min.

Preferably, the crystalline form (Form 1) of vadadustat L-proline of the present invention as defined in any one of the embodiments described above is an anhydrous form.

Even more preferably, the crystalline form (Form 1) of vadadustat L-proline of the present invention as defined in any one of the embodiments described above is a non-solvated form.

In another aspect, the present invention relates to a composition comprising the crystalline form (Form 1) of vadadustat L-proline of the present invention as defined in any one of the embodiments described above, said composition being essentially free of any other solid-state form of vadadustat. For example, the composition comprises at most 20 weight %, preferably at most 10 weight %, more preferably at most 5 weight %, 4 weight %, 3 weight %, 2 weight % or 1 weight % of any other solid-state form of vadadustat, based on the weight of the composition. Preferably, the any other solid-state form of vadadustat is selected from the group consisting of Form A, Form B and Form C of WO 2015/073779 A1, Form CS1 and CS8 of WO 2018/108101 A1 and amorphous vadadustat. Most preferably, the any other solid-state form of vadadustat is Form A and/or Form B.

Vadadustat Form A of WO 2015/073779 A1 is characterized by having a PXRD comprising amongst others a characteristic reflection at 2-Theta angles of (20.3±0.2)°, when measured at a temperature in the range of from 20 to 30° C. with Cu-Kalpha$_{1,2}$ radiation having a wavelength of 0.15419 nm, whereas the PXRD of vadadustat L-proline form 1 of the present invention displays no reflections in the same range. Therefore, the absence of reflections at 2-Theta angles of (20.3±0.2)° confirms the absence of vadadustat form A in the composition comprising vadadustat L-proline form 1.

Hence, in a preferred embodiment, the present invention relates to a composition comprising the crystalline form (Form 1) of vadadustat L-proline of the present invention as defined in any one of the embodiments described above, characterized by having a PXRD comprising no reflections at 2-Theta angles of (20.3±0.2)°, when measured at a temperature in the range of from 20 to 30° C. with Cu-Kalpha$_{1,2}$ radiation having a wavelength of 0.15419 nm.

Vadadustat Form B of WO 2015/073779 A1 is characterized by a having a PXRD comprising amongst others a characteristic reflection at 2-Theta angles of (15.3±0.2)°, when measured at a temperature in the range of from 20 to 30° C. with Cu-Kalpha$_{1,2}$ radiation having a wavelength of 0.15419 nm, whereas the PXRD of vadadustat L-proline form 1 of the present invention displays no reflections in the same range. Therefore, the absence of reflections at 2-Theta angles of (15.3±0.2)° confirms the absence of vadadustat form B in the composition comprising vadadustat L-proline form 1.

Hence, in another preferred embodiment, the present invention relates to a composition comprising the crystalline form (Form 1) of vadadustat L-proline of the present invention as defined in any one of the embodiments described above, characterized by having a PXRD comprising no reflections at 2-Theta angles of (15.3±0.2)°, when measured at a temperature in the range of from 20 to 30° C. with Cu-Kalpha$_{1,2}$ radiation having a wavelength of 0.15419 nm.

Even more preferably, the present invention relates to a composition comprising the crystalline form (Form 1) of vadadustat and L-proline of the present invention as defined in any one of the embodiments described above, characterized by having a PXRD comprising no reflections at 2-Theta angles of (15.3±0.2)° and (20.3±0.2)°, when measured at a temperature in the range of from 20 to 30° C. with Cu-Kalpha$_{1,2}$ radiation having a wavelength of 0.15419 nm.

Furthermore, the invention relates to a composition comprising the crystalline form (Form 1) of vadadustat L-proline of the present invention as defined in any one of the embodiments described above, characterized in that the composition is essentially free of a compound of Formula (III)

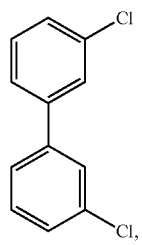

Formula (III)

as determined by GC/MS.

For example, the composition comprises at most 100 ppm, preferably at most 75 ppm, more preferably at most 50 ppm, even more preferably at most 25 ppm, most preferably at most 10 ppm or 5 ppm, for example at most 4, 3, 2 or 1 ppm of a compound of Formula (III), as determined by GC/MS.

In a further aspect, the present invention relates to a process for the preparation of the crystalline form (Form 1) of vadadustat and L-proline of the present invention as defined in any one of the embodiments described above comprising:
(a) dissolving vadadustat and L-proline in a solvent mixture comprising methanol and THF;
(b) crystallizing vadadustat L-proline;
(c) separating at least a part of the crystals obtained in (b) from the mother liquor;
(d) optionally, washing the isolated crystals obtained in (c); and
(e) drying the crystals obtained in any one of steps (b) to (d).

Vadadustat can for example be prepared according to the procedures disclosed in WO 2008/002576 A2 and WO 2012/170377 A1, respectively. Vadadustat may be applied as crystalline material in step (a) of the above described procedure. Suitable crystalline forms which may be used are for example forms A, B and C of WO 2015/073779 A1, forms CS1, CS2 and CS3 of WO 2018/108101 A1 or the 1,4-dioxane solvate described herein (see reference example 1).

The volume ratio of methanol and THF of the solvent mixture is about 1:1. The vadadustat concentration in step (a) is in the range of from about 50 to 80 g/L, most preferably from about 60-70 g/L solvent mixture. The molar ratio of vadadustat and L-proline applied is in the range of from 1.0:1.5 to 1.0:2.0. In order to achieve dissolution, the mixture is preferably heated until the solids dissolve e.g. to reflux temperature or below.

In order to initiate crystallization, the solution is kept at room temperature, preferably under stirring. Optionally, vadadustat L-proline form 1 may be added as seeds in order to promote crystallization and/or to control particle size distribution. The amount of seed crystals employed may range from about 1 to 20 weight %, preferably from about 1 to 10 weight % and most preferably from about 1 to 5 weight %, based on the weight of applied vadadustat starting material. Seed crystals may be prepared according to steps (a) to (b) of the above described procedure e.g. according to the procedure disclosed in example 1 of the present invention.

The obtained suspension may optionally be further slurried, preferably at room temperature. Slurrying encompasses any kind of movement of the solid material suspended in water caused by, but not limited to e.g. agitation, stirring, mixing, shaking, vibration, sonication, wet milling and the like. Slurrying may be conducted for a time sufficient that at least a substantial part, preferably all of the vadadustat starting material has converted to the vadadustat L-proline form 1 of the present invention. Preferably slurrying is performed for a period in the range of from several hours to several days. Slurrying may for example be performed for a period in the range of from 2 hours to 7 days. The skilled person may monitor the conversion of vadadustat to the vadadustat L-proline form 1 of the present invention by withdrawing samples from the slurry and analyzing the samples by e.g. powder X-ray diffraction.

Once vadadustat L-proline form 1 of the present invention is obtained or preferably obtained in essentially pure form, at least a part of the crystals are separated from the mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with a solvent mixture comprising methanol and THF, wherein the volume ratio of methanol and THF of the solvent mixture is about 1:1.

The obtained crystals are then dried. Drying may be performed at a temperature in the range of from about 20 to 80° C., preferably in the range of from about 20 to 40° C. and most preferably drying is performed at RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 10 mbar may be applied for drying.

Vadadustat L-Proline Form 2

In another embodiment the invention relates to a crystalline form (Form 2) of vadadustat L-proline, characterized by having a PXRD comprising reflections at 2-Theta angles of:
- $(8.4\pm0.2)°$, $(15.7\pm0.2)°$ and $(16.2\pm0.2)°$; or
- $(5.2\pm0.2)°$, $(8.4\pm0.2)°$, $(15.7\pm0.2)°$ and $(16.2\pm0.2)°$; or
- $(5.2\pm0.2)°$, $(8.4\pm0.2)°$, $(15.7\pm0.2)°$, $(16.2\pm0.2)°$ and $(19.3\pm0.2)°$; or
- $(5.2\pm0.2)°$, $(8.4\pm0.2)°$, $(15.7\pm0.2)°$, $(16.2\pm0.2)°$, $(19.3\pm0.2)°$ and $(26.1\pm0.2)°$; or
- $(5.2\pm0.2)°$, $(8.4\pm0.2)°$, $(15.7\pm0.2)°$, $(16.2\pm0.2)°$, $(19.3\pm0.2)°$, $(21.1\pm0.2)°$ and $(26.1\pm0.2)°$; or
- $(5.2\pm0.2)°$, $(8.4\pm0.2)°$, $(15.7\pm0.2)°$, $(16.2\pm0.2)°$, $(19.3\pm0.2)°$, $(21.1\pm0.2)°$, $(23.3\pm0.2)°$ and $(26.1\pm0.2)°$; or
- $(5.2\pm0.2)°$, $(8.4\pm0.2)°$, $(15.7\pm0.2)°$, $(16.2\pm0.2)°$, $(18.1\pm0.2)°$, $(19.3\pm0.2)°$, $(21.1\pm0.2)°$, $(23.3\pm0.2)°$ and $(26.1\pm0.2)°$; or
- $(5.2\pm0.2)°$, $(8.4\pm0.2)°$, $(12.9\pm0.2)°$, $(15.7\pm0.2)°$, $(16.2\pm0.2)°$, $(18.1\pm0.2)°$, $(19.3\pm0.2)°$, $(21.1\pm0.2)°$, $(23.3\pm0.2)°$ and $(26.1\pm0.2)°$, when measured at RT with Cu-Kalpha$_{1,2}$ radiation having a wavelength of 0.15419 nm.

Alternatively, the invention relates to a crystalline form (Form 2) of vadadustat L-proline, characterized by having a PXRD comprising reflections at 2-Theta angles of:
- $(8.4\pm0.1)°$, $(15.7\pm0.1)°$ and $(16.2\pm0.1)°$; or
- $(5.2\pm0.1)°$, $(8.4\pm0.1)°$, $(15.7\pm0.1)°$ and $(16.2\pm0.1)°$; or
- $(5.2\pm0.1)°$, $(8.4\pm0.1)°$, $(15.7\pm0.1)°$, $(16.2\pm0.1)°$ and $(19.3\pm0.1)°$; or
- $(5.2\pm0.1)°$, $(8.4\pm0.1)°$, $(15.7\pm0.1)°$, $(16.2\pm0.1)°$, $(19.3\pm0.1)°$ and $(26.1\pm0.1)°$; or
- $(5.2\pm0.1)°$, $(8.4\pm0.1)°$, $(15.7\pm0.1)°$, $(16.2\pm0.1)°$, $(19.3\pm0.1)°$, $(21.1\pm0.1)°$ and $(26.1\pm0.1)°$; or
- $(5.2\pm0.1)°$, $(8.4\pm0.1)°$, $(15.7\pm0.1)°$, $(16.2\pm0.1)°$, $(19.3\pm0.1)°$, $(21.1\pm0.1)°$, $(23.3\pm0.1)°$ and $(26.1\pm0.1)°$; or
- $(5.2\pm0.1)°$, $(8.4\pm0.1)°$, $(15.7\pm0.1)°$, $(16.2\pm0.1)°$, $(18.1\pm0.1)°$, $(19.3\pm0.1)°$, $(21.1\pm0.1)°$, $(23.3\pm0.1)°$ and $(26.1\pm0.1)°$; or
- $(5.2\pm0.1)°$, $(8.4\pm0.1)°$, $(12.9\pm0.1)°$, $(15.7\pm0.1)°$, $(16.2\pm0.1)°$, $(18.1\pm0.1)°$, $(19.3\pm0.1)°$, $(21.1\pm0.1)°$, $(23.3\pm0.1)°$ and $(26.1\pm0.1)°$, when measured at a temperature in the range of from 20 to 30° C. with Cu-Kalpha$_{1,2}$ radiation having a wavelength of 0.15419 nm.

Figure 5:
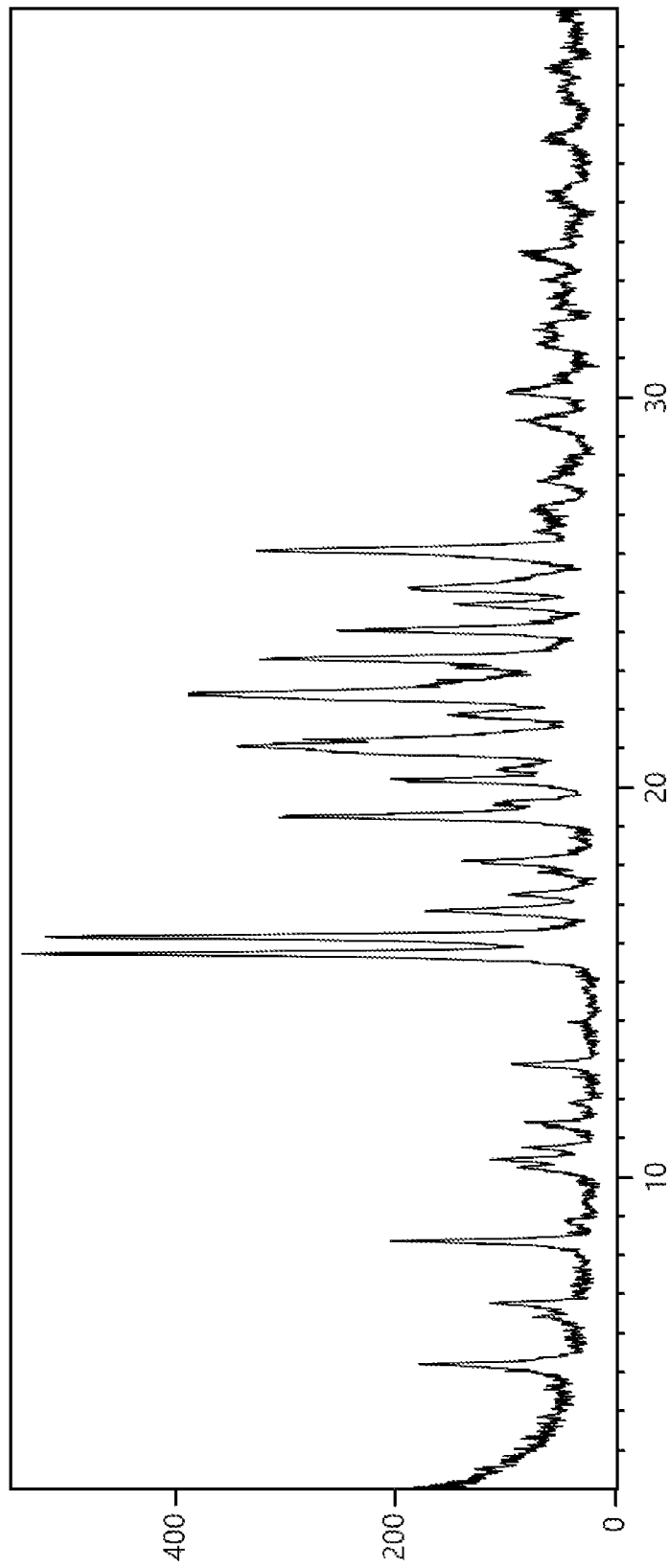
FIG. 5: illustrates a representative PXRD of vadadustat L-proline Form 2 according to the present invention. The x-axis shows the scattering angle in ° 2-Theta, the y-axis shows the intensity of the scattered X-ray beam in counts of detected photons.

Also, the invention relates to a crystalline form (Form 2) of vadadustat L-proline, characterized by having a PXRD essentially the same as shown in FIG. 5 of the present invention, when measured at RT with Cu-Kalpha$_{1,2}$ radiation having a wavelength of 0.15419 nm.

In addition, the present invention relates to a crystalline form (Form 2) of vadadustat L-proline, characterized by having an FTIR spectrum comprising peaks at wavenumbers of:
- $(3383\pm4)$ cm$^{-1}$, $(3130\pm4)$ cm$^{-1}$ and $(1718\pm4)$ cm$^{-1}$ or;
- $(3383\pm4)$ cm$^{-1}$, $(3130\pm4)$ cm$^{-1}$, $(1718\pm4)$ cm$^{-1}$ and $(1649\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$ and $(1530\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$, $(1530\pm4)$ cm$^{-1}$ and $(1384\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$, $(1530\pm4)$ cm$^{-1}$, $(1384\pm4)$ cm$^{-1}$ and $(1215\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$, $(1530\pm4)$ cm$^{-1}$, $(1384\pm4)$ cm$^{-1}$, $(1215\pm4)$ cm$^{-1}$ and $(760\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$, $(1530\pm4)$ cm$^{-1}$, $(1384\pm4)$ cm$^{-1}$, $(1325\pm4)$ cm$^{-1}$, $(1215\pm4)$ cm$^{-1}$ and $(760\pm4)$ cm$^{-1}$; or
- $(3383\pm4)$ cm$^{-1}$, $(3130\pm4)$ cm$^{-1}$, $(1718\pm4)$ cm$^{-1}$, $(1649\pm4)$ cm$^{-1}$, $(1585\pm4)$ cm$^{-1}$, $(1530\pm4)$ cm$^{-1}$, $(1384\pm4)$ cm$^{-1}$, $(1325\pm4)$ cm$^{-1}$, $(1215\pm4)$ cm$^{-1}$ and $(760\pm4)$ cm$^{-1}$, when measured at RT with a diamond ATR cell.

Alternatively, the present invention relates to a crystalline form (Form 2) of vadadustat L-proline, characterized by having an FTIR spectrum comprising peaks at wavenumbers of:
- $(3383\pm2)$ cm$^{-1}$, $(3130\pm2)$ cm$^{-1}$ and $(1718\pm2)$ cm$^{-1}$ or;
- $(3383\pm2)$ cm$^{-1}$, $(3130\pm2)$ cm$^{-1}$, $(1718\pm2)$ cm$^{-1}$ and $(1649\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$ and $(1530\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$, $(1530\pm2)$ cm$^{-1}$ and $(1384\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$, $(1530\pm2)$ cm$^{-1}$, $(1384\pm2)$ cm$^{-1}$ and $(1215\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$, $(1530\pm2)$ cm$^{-1}$, $(1384\pm2)$ cm$^{-1}$, $(1215\pm2)$ cm$^{-1}$ and $(760\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$, $(1530\pm2)$ cm$^{-1}$, $(1384\pm2)$ cm$^{-1}$, $(1325\pm2)$ cm$^{-1}$, $(1215\pm2)$ cm$^{-1}$ and $(760\pm2)$ cm$^{-1}$; or
- $(3383\pm2)$ cm$^{-1}$, $(3130\pm2)$ cm$^{-1}$, $(1718\pm2)$ cm$^{-1}$, $(1649\pm2)$ cm$^{-1}$, $(1585\pm2)$ cm$^{-1}$, $(1530\pm2)$ cm$^{-1}$, $(1384\pm2)$ cm$^{-1}$, $(1325\pm2)$ cm$^{-1}$, $(1215\pm2)$ cm$^{-1}$ and $(760\pm2)$ cm$^{-1}$, when measured at RT with a diamond ATR cell.

Figure 6:
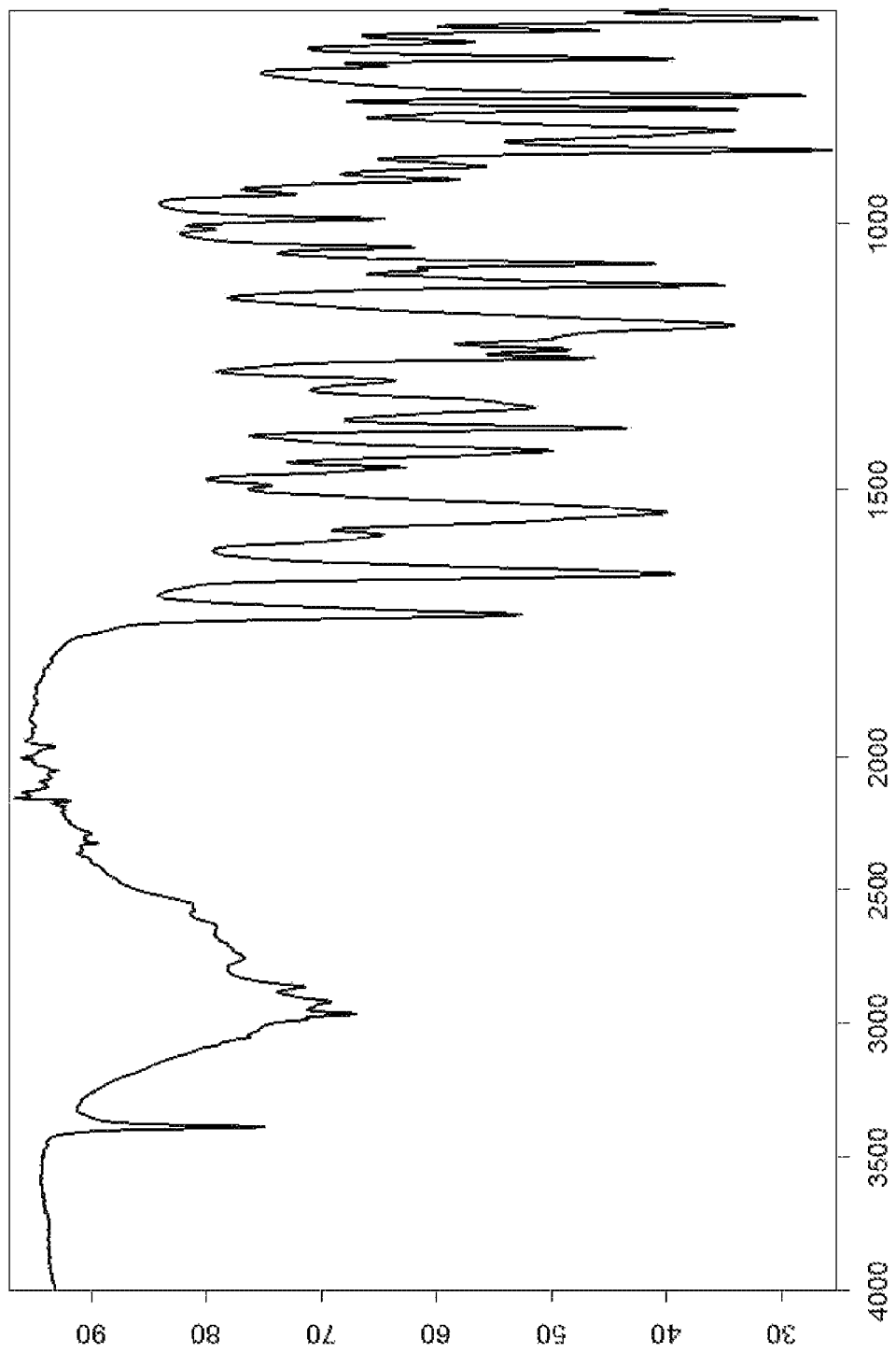
FIG. 6: illustrates a representative FTIR spectrum of vadadustat L-proline Form 2 according to the present invention. The x-axis shows the wavenumbers in $cm^{-1}$, the y-axis shows the relative intensity in percent transmittance.

Moreover, the present invention relates to a crystalline form (Form 2) of vadadustat L-proline, characterized by having an FTIR spectrum essentially the same as shown in FIG. 6 of the present invention, when measured at RT with a diamond ATR cell.

In another embodiment, the present invention relates to a crystalline form (Form 2) of vadadustat L-proline, characterized by having a DSC curve comprising an endothermic peak, preferably a single endothermic peak, having an onset at a temperature in the range of from $(178\pm5)°$ C., preferably of from $(178\pm3)°$ C., more preferably of from $(178\pm2)°$ C., even more preferably of from $(178\pm1)°$ C., for example having an onset at a temperature of about 178° C., when measured with DSC at a heating rate of 10 K/min.

In a further embodiment, the present invention relates to a crystalline form (Form 2) of vadadustat L-proline, characterized by having a DSC curve comprising an endothermic peak, preferably a single endothermic peak, having a peak maximum at a temperature in the range of from (179±5)° C., preferably of from (179±3)° C., more preferably of from (179±2)° C., even more preferably of from (179±1)° C., for example having a peak maximum at a temperature of about 179° C., when measured with DSC at a heating rate of 10 K/min.

In still another embodiment, the invention relates to a crystalline form (Form 2) of vadadustat L-proline, characterized by having a melting point onset at a temperature in the range of from (178±5)° C., preferably of from (178±3)° C., more preferably of from (178±2)° C., even more preferably of from (178±1)° C., for example having a melting point onset at a temperature of about 178° C., when measured with DSC at a heating rate of 10 K/min.

In another embodiment, the present invention relates to a crystalline form (Form 2) of vadadustat L-proline, characterized by having a TGA curve showing a mass loss of not more than 0.5 weight %, preferably of not more than 0.2 weight % based on the weight of the crystalline form, when heated from 25 to 170° C. at a rate of 10 K/min.

Preferably, the crystalline form (Form 2) of vadadustat L-proline of the present invention as defined in any one of the embodiments described above is an anhydrous form.

Even more preferably, the crystalline form (Form 2) of vadadustat L-proline of the present invention as defined in any one of the embodiments described above is a non-solvated form.

In another aspect, the present invention relates to a composition comprising the crystalline form (Form 2) of vadadustat L-proline of the present invention as defined in any one of the embodiments described above, said composition being essentially free of any other solid-state form of vadadustat. For example, the composition comprises at most 20 weight %, preferably at most 10 weight %, more preferably at most 5 weight %, 4 weight %, 3 weight %, 2 weight % or 1 weight % of any other solid-state form of vadadustat, based on the weight of the composition. Preferably, the any other solid-state form of vadadustat is selected from the group consisting of Form A, Form B and Form C of WO 2015/073779 A1, Form CS1 and CS8 of WO 2018/108101 A1 and amorphous vadadustat. Most preferably, the any other solid-state form of vadadustat is Form A and/or Form B.

Vadadustat Form A of WO 2015/073779 A1 is characterized by having a PXRD comprising amongst others a characteristic reflection at 2-Theta angles of (15.0±0.2)°, when measured at a temperature in the range of from 20 to 30° C. with Cu-Kalpha$_{1,2}$ radiation having a wavelength of 0.15419 nm, whereas the PXRD of vadadustat L-proline form 2 of the present invention displays no reflections in the same range. Therefore, the absence of reflections at 2-Theta angles of (15.0±0.2)° confirms the absence of vadadustat form A in the composition comprising vadadustat L-proline form 2.

Hence, in a preferred embodiment, the present invention relates to a composition comprising the crystalline form (Form 2) of vadadustat L-proline of the present invention as defined in any one of the embodiments described above, characterized by having a PXRD comprising no reflections at 2-Theta angles of (15.0±0.2)°, when measured at a temperature in the range of from 20 to 30° C. with Cu-Kalpha$_{1,2}$ radiation having a wavelength of 0.15419 nm.

Vadadustat Form B of WO 2015/073779 A1 is characterized by a having a PXRD comprising amongst others a characteristic reflection at 2-Theta angles of (15.3±0.2)°, when measured at a temperature in the range of from 20 to 30° C. with Cu-Kalpha$_{1,2}$ radiation having a wavelength of 0.15419 nm, whereas the PXRD of vadadustat L-proline form 2 of the present invention displays no reflections in the same range. Therefore, the absence of reflections at 2-Theta angles of (15.3±0.2)° confirms the absence of vadadustat form B in the composition comprising vadadustat L-proline form 2.

Hence, in another preferred embodiment, the present invention relates to a composition comprising the crystalline form (Form 2) of vadadustat L-proline of the present invention as defined in any one of the embodiments described above, characterized by having a PXRD comprising no reflections at 2-Theta angles of (15.3±0.2)°, when measured at a temperature in the range of from 20 to 30° C. with Cu-Kalpha$_{1,2}$ radiation having a wavelength of 0.15419 nm.

Even more preferably, the present invention relates to a composition comprising the crystalline form (Form 2) of vadadustat and L-proline of the present invention as defined in any one of the embodiments described above, characterized by having a PXRD comprising no reflections at 2-Theta angles of (15.0±0.2)° and (15.3±0.2)°, when measured at a temperature in the range of from 20 to 30° C. with Cu-Kalpha$_{1,2}$ radiation having a wavelength of 0.15419 nm.

Furthermore, the invention relates to a composition comprising the crystalline form (Form 2) of vadadustat L-proline of the present invention as defined in any one of the embodiments described above, characterized in that the composition is essentially free of a compound of Formula (III)

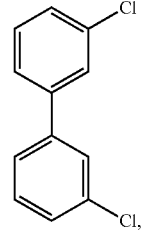

Formula (III)

as determined by GC/MS.

For example, the composition comprises at most 100 ppm, preferably at most 75 ppm, more preferably at most 50 ppm, even more preferably at most 25 ppm, most preferably at most 10 ppm or 5 ppm, for example at most 4, 3, 2 or 1 ppm of a compound of Formula (III), as determined by GC/MS.

In a further aspect, the present invention relates to a process for the preparation of the crystalline form (Form 2) of vadadustat and L-proline of the present invention as defined in any one of the embodiments described above comprising:
 (a) providing a mixture comprising vadadustat and L-proline in a solvent, wherein the solvent is selected from a $C_1$-$C_3$ alcohol;
 (b) crystallizing vadadustat L-proline;
 (c) separating at least a part of the crystals obtained in (b) from the mother liquor;
 (d) optionally, washing the isolated crystals obtained in (c); and (e) drying the crystals obtained in any one of steps (b) to (d).

Vadadustat can for example be prepared according to the procedures disclosed in WO 2008/002576 A1 and WO 2012/170377 A2, respectively. Vadadustat may be applied as crystalline material in step (a) of the above described procedure. Suitable crystalline forms which may be used are for example forms A, B and C of WO 2015/073779 A1, forms CS1, CS2 and CS3 of WO 2018/108101 A1 or the 1,4-dioxane solvate described herein (see reference example 1).

The $C_1$-$C_3$ alcohol applied in step (a) may be selected from the group consisting of methanol, ethanol, 1-propanol and 2-propanol, wherein 2-propanol is most preferred. Depending on the solvent applied, the vadadustat concentration in step (a) is in the range of from about 30 to 70 g/L, most preferably from about 40-60 g/L solvent. The molar ratio of vadadustat and L-proline applied is in the range of from 1.0:0.8 to 1.0 to 1.2, preferably 1.0:1.0. In order to achieve dissolution, the mixture is preferably heated until the solids dissolve e.g. to reflux temperature or below. The mixture may also remain a suspension.

In order to initiate crystallization, the solution is kept at room temperature, preferably under stirring. Optionally, vadadustat L-proline form 2 may be added as seeds in order to promote crystallization and/or to control particle size distribution. The amount of seed crystals employed may range from about 1 to 20 weight %, preferably from about 1 to 10 weight % and most preferably from about 1 to 5 weight %, based on the weight of applied vadadustat starting material. Seed crystals may be prepared according to steps (a) to (b) of the above described procedure e.g. according to the procedure disclosed in example 2 of the present invention.

The suspension may optionally be further slurried, preferably at room temperature. Slurrying encompasses any kind of movement of the solid material suspended in water caused by, but not limited to e.g. agitation, stirring, mixing, shaking, vibration, sonication, wet milling and the like. Slurrying may be conducted for a time sufficient that at least a substantial part, preferably all of the vadadustat starting material has converted to the vadadustat L-proline form 2 of the present invention. Preferably slurrying is performed for a period in the range of from several hours to several days. Slurrying may for example be performed for a period in the range of from 2 hours to 7 days. The skilled person may monitor the conversion of vadadustat to the vadadustat L-proline form 2 of the present invention by withdrawing samples from the slurry and analyzing the samples by e.g. powder X-ray diffraction.

Once vadadustat L-proline form 2 of the present invention is obtained or preferably obtained in essentially pure form, at least a part of the crystals are separated from the mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with the $C_1$-$C_3$ alcohol applied in step (a).

The obtained crystals are then dried. Drying may be performed at a temperature in the range of from about 20 to 80° C., preferably in the range of from about 20 to 40° C. and most preferably drying is performed at RT. Drying may be performed for a period in the range of from about 1 to 72 hours, preferably of from about 2 to 48 hours, more preferably of from about 4 to 24 hours and most preferably of from about 6 to 18 hours. Drying may be performed at ambient pressure and/or under reduced pressure. Preferably, drying is performed at a pressure of about 100 mbar or less, more preferably of about 50 mbar or less and most preferably of about 30 mbar or less, for example a vacuum of about 10 mbar may be applied for drying.

Pharmaceutical Composition and Medical Use

The present invention relates to the use of the crystalline form 1 of vadadustat L-proline or a composition comprising the same as defined in any one of the above described embodiments or the use of the crystalline form 2 of vadadustat L-proline or a composition comprising the same as defined in any one of the above described embodiments for the preparation of a pharmaceutical composition.

In addition, the invention relates to a pharmaceutical composition comprising the crystalline form 1 of vadadustat L-proline or a composition comprising the same as defined in any one of the above described embodiments or the crystalline form 2 of vadadustat L-proline or a composition comprising the same as defined in any one of the above described embodiments, preferably in an effective and/or predetermined amount, and at least one pharmaceutically acceptable excipient.

Preferably, the predetermined and/or effective amount of crystalline form 1 of vadadustat L-proline or crystalline form 2 of vadadustat L-proline of the present invention is in the range of from 40 to 315 mg calculated as vadadustat. For example, the predetermined and/or effective amount is selected from the group consisting of about 40 mg, 120 mg, 150 mg, 185 mg, 200 mg, 250 mg, 300 mg and 315 mg calculated as vadadustat and preferably the predetermined and/or effective amount is about 150 mg calculated as vadadustat.

Preferably, the pharmaceutical composition of the present invention as described above is an oral solid dosage form. In particular, the pharmaceutical composition of the present invention as describe above is a tablet, preferably a film-coated tablet.

For example, the invention relates to an oral solid dosage form comprising intra-granular components and extra-granular components, and film coating components, wherein the intra-granular components comprise crystalline form 1 of vadadustat L-proline or crystalline form 2 of vadadustat L-proline, an insoluble diluent or carrier, a disintegrant, and a diluent or filler, the extra-granular components comprise a disintegrant, a glidant, and/or a lubricant and the film coating components comprise a tablet coating.

In particular, the invention relates to an oral solid dosage form comprising intra-granular components and extra-granular components, and film coating components, wherein the intra-granular components comprise crystalline form 1 of vadadustat L-proline or crystalline form 2 of vadadustat L-proline, microcrystalline cellulose, sodium starch glycolate and hydroxypropyl methylcellulose, the extra-granular components comprise sodium starch glycolate, colloidal silicon dioxide and magnesium stearate, and the film coating components comprise Opadry®.

Moreover, the present invention relates to crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments for use as a medicament.

In addition, the present invention relates to crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments for use in the treatment and/or prevention of anemia. For example, anemia is selected from the group consisting of iron deficiency anemia, sickle cell anemia, constitutional aplastic anemia, unspecified aplastic anemia, non-autoimmune haemolytic anemia, anemia complicating pregnancy, childbirth or the puerperium, pernicious anemia, nutritional anemia, autoimmune haemolytic anemia and anemia due to enzyme deficiency, congestive heart failure (CHF), chronic kidney disease (CKD), myelodysplastic syndrome, pregnancy, Crohn's disease, regional enteritis, inflammatory bowel disease (IBS), ulcerative colitis, ulcerative proctitis, idiopathic proctocolitis, myocardial infarction (MI), heart attack, systemic lupus erythematosus (SLE), agranulocytosis, cancer, end stage renal disease (ESRD), chronic obstructive pulmonary disease (COPD), rheumatoid arthritis (RA), acute renal failure (ARF), pneumonia and pulmonary artery hypertension.

In particular, the invention relates to crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments for use in the treatment and/or prophylaxis of anemia in patients with end-stage renal disease (ESRD) and/or chronic kidney disease (CKD). Even more preferably, patients include both dialysis dependent and non-dialysis dependent patients.

The invention also concerns a method of treating and/or preventing anemia, said method comprising administering an effective amount of crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments to a patient in need of such a treatment.

In addition, the invention concerns a method of treating and/or preventing anemia in patients with end-stage renal disease (ESRD) and/or chronic kidney disease (CKD), said method comprising administering an effective amount of crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments to a patient in need of such a treatment.

Furthermore, the invention concerns a method of treating and/or preventing anemia in patients with end-stage renal disease (ESRD) and/or chronic kidney disease (CKD), including patients who are both dialysis dependent and non-dialysis dependent, said method comprising administering an effective amount of crystalline form 1 of vadadustat L-proline or a composition comprising the same, crystalline form 2 of vadadustat L-proline or a composition comprising the same or the pharmaceutical composition, as defined in any one of the above described aspects and their corresponding embodiments to a patient in need of such a treatment.

EXAMPLES

The following non-limiting examples are illustrative for the disclosure and are not to be construed as to be in any way limiting for the scope of the invention.

Powder X-Ray Diffraction

Powder X-ray diffraction was performed with a PANalytical X'Pert PRO diffractometer equipped with a theta/theta coupled goniometer in transmission geometry, Cu-Kalpha$_{1,2}$ radiation (wavelength 0.15419 nm) with a focusing mirror and a solid state PIXcel detector. Diffractograms were recorded at a tube voltage of 45 kV and a tube current of 40 mA, applying a stepsize of 0.013° 2-theta with 40s per step (255 channels) in the angular range of 2° to 40° 2-Theta at ambient conditions. A typical precision of the 2-Theta values is in the range of ±0.2° 2-Theta, preferably of ±0.1° 2-Theta. Thus, for example the diffraction peak of the Form 1 vadadustat L-proline co-crystal of the present invention at 8.2° 2-Theta can appear in the range of from 8.0 to 8.4° 2-Theta, preferably in the range of from 8.1 to 8.3° 2-Theta on most X-ray diffractometers under standard conditions.

Fourier Transform Infrared Spectroscopy

FTIR spectra were recorded (obtained) on a MKII Golden Gate™ Single Reflection Diamond ATR cell with a Bruker Tensor 27 FTIR spectrometer with 4 cm$^{-1}$ resolution at RT. To record a spectrum a spatula tip of the sample was applied to the surface of the diamond in powder form. Then the sample was pressed onto the diamond with a sapphire anvil and the spectrum was recorded. A spectrum of the clean diamond was used as background spectrum. A typical precision of the wavenumber values is in the range of from about ±4 cm$^{-1}$, preferably of from ±2 cm$^{-1}$. Thus, the infrared peak of vadadustat L-proline form 1 according to the present invention at 3378 cm$^{-1}$ can appear between 3374 and 3382 cm$^{-1}$, preferably between 3376 and 3380 cm$^{-1}$ on most infrared spectrometers under standard conditions.

Differential Scanning Calorimetry

DSC was performed on a Mettler Polymer DSC R instrument. The samples (5.61 mg Form 1 and 3.89 mg Form 2, 4.07 mg 1,4-dioxane solvate) were heated in a 40 microliter aluminium pan with a pierced aluminium lid from 25 to 250° C. at a rate of 10 K/min. Nitrogen (purge rate 50 mL/min) was used as purge gas.

Thermogravimetric Analyses

TGA was performed on a Mettler TGA/DSC 1 instrument. The samples (9.53 mg Form 1 and 8.16 mg Form 2, 8.12 mg 1,4-dioxane solvate) were heated in a 100 microliter aluminum pan closed with an aluminum lid. The lid was automatically pierced at the beginning of the measurement. The samples were heated from 25 to 250° C. at a rate of 10 K/min. Nitrogen (purge rate 50 mL/min) was used as purge gas.

Example 1: Preparation of Vadadustat L-Proline Form 1

Vadadustat (134 mg, 437 mmol, e.g. prepared according to the procedure disclosed in Example 4 of WO 2012/170377 A1) and L-proline (101 mg, 877 mmol) were dissolved in a mixture of methanol (1 mL) and THF (1 mL) upon heating to 65° C. The obtained clear solution was cooled to 20° C. at a rate of −3 K/min, whereat crystallization occurred. The resulting suspension was stirred for 18 hours at 20° C., the solid was collected by filtration and dried for 24 hours at room temperature under vacuum (~10 mbar) to obtain vadadustat L-proline form 1.

Yield: 95 mg

Powder X-Ray Diffraction

A representative diffractogram of vadadustat L-proline form 1 according to the present invention is displayed in FIG. 1 and the corresponding reflection list (peak list) from 2 to 30° 2-Theta is provided in table 1 below.

TABLE 1

Reflection (peak) positions of vadadustat L-proline form 1
according to the present invention in the range of from 2 to 30°
2-Theta; A typical precision of the 2-Theta values is in the range
of ±0.2° 2-Theta, preferably of ±0.1° 2-Theta.

| Reflection position [° 2-Theta] |
|---|
| 8.2 |
| 11.2 |
| 11.9 |
| 16.4 |
| 17.9 |
| 18.8 |
| 19.3 |
| 19.6 |
| 21.6 |
| 21.8 |
| 22.5 |
| 23.0 |
| 23.4 |
| 24.0 |
| 24.7 |
| 25.2 |
| 25.5 |
| 26.1 |
| 26.9 |
| 27.9 |
| 29.4 |

Fourier Transform Infrared Spectroscopy

A representative FTIR spectrum of the vadadustat L-proline form 1 according to the present invention is displayed in FIG. 2 and the corresponding peak list is provided in table 2 below.

TABLE 2

FTIR peak list of vadadustat L-proline form 1 according to
the present invention; a typica precision of the wavenumbers
is in the range of ±4 $cm^{-1}$, preferably of ±2 $cm^{-1}$.

| Wavenumber [$cm^{-1}$] |
|---|
| 3378 |
| 3217 |
| 3057 |
| 2985 |
| 1982 |
| 1718 |
| 1651 |
| 1616 |
| 1596 |
| 1559 |
| 1532 |
| 1461 |
| 1436 |
| 1380 |
| 1314 |
| 1192 |
| 1172 |
| 1086 |
| 1037 |
| 994 |
| 954 |
| 926 |
| 894 |
| 824 |
| 790 |
| 759 |
| 687 |
| 660 |
| 625 |

Differential Scanning Calorimetry

Figure 3:
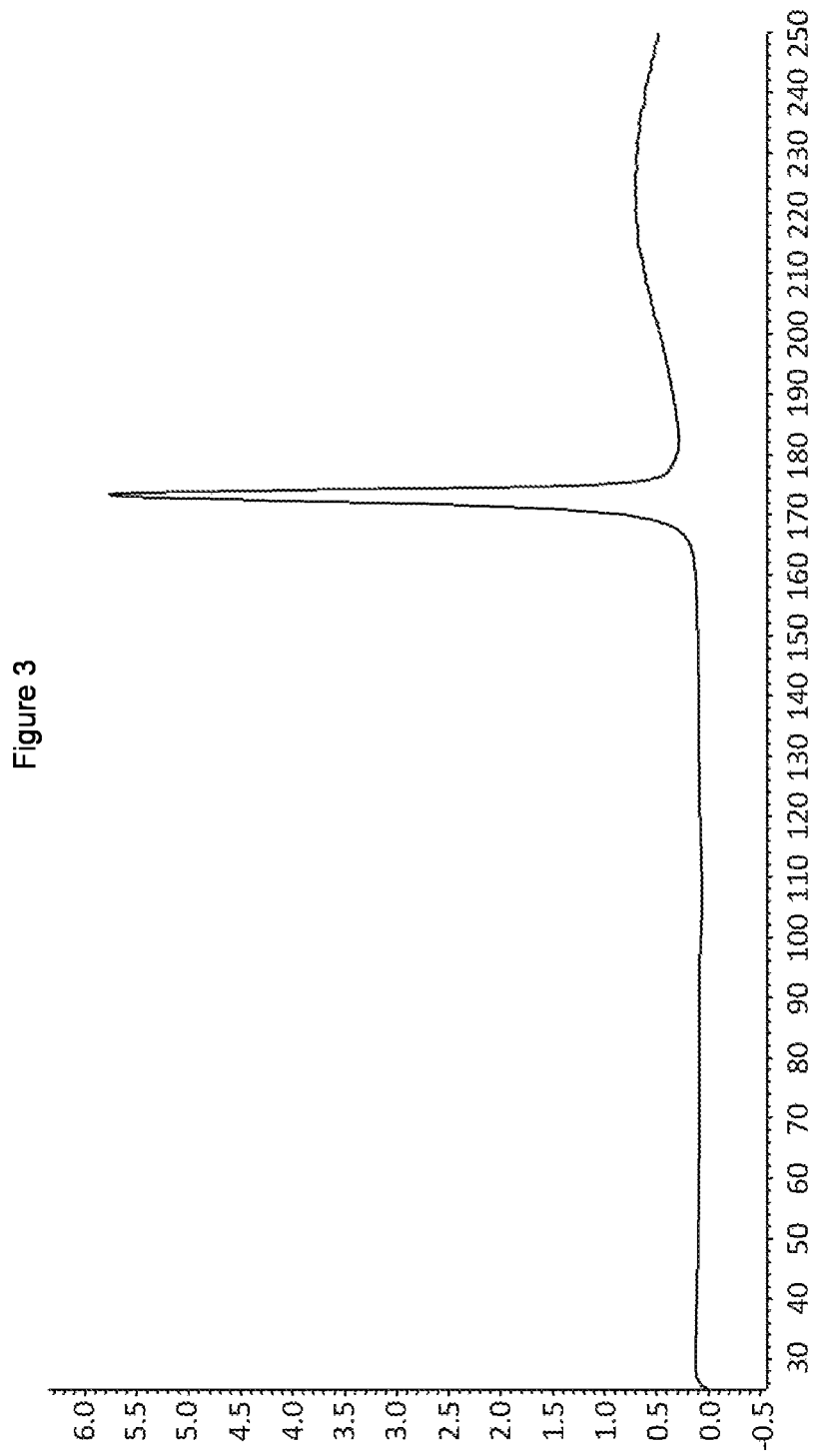
FIG. 3: illustrates a representative DSC curve of vadadustat L-proline Form 1 according to the present invention. The x-axis shows the temperature in degree Celsius (° C.), the y-axis shows the heat flow rate in Watt per gram (W/g) with endothermic peaks going up.

The DSC curve of vadadustat L-proline form 1 of the present invention, which is displayed in FIG. 3 herein, shows a single endothermic peak with an onset at a temperature of about 170° C., a peak at a temperature of about 172° C. and an enthalpy of about 98 J/g, which is due to the melting of the crystalline form. No other thermal are visible until the crystalline form melts, indicating that vadadustat L-proline form 1 of the present invention undergoes no desolvation or phase transformations but is stable until it melts.

Thermogravimetric Analysis

Figure 4:
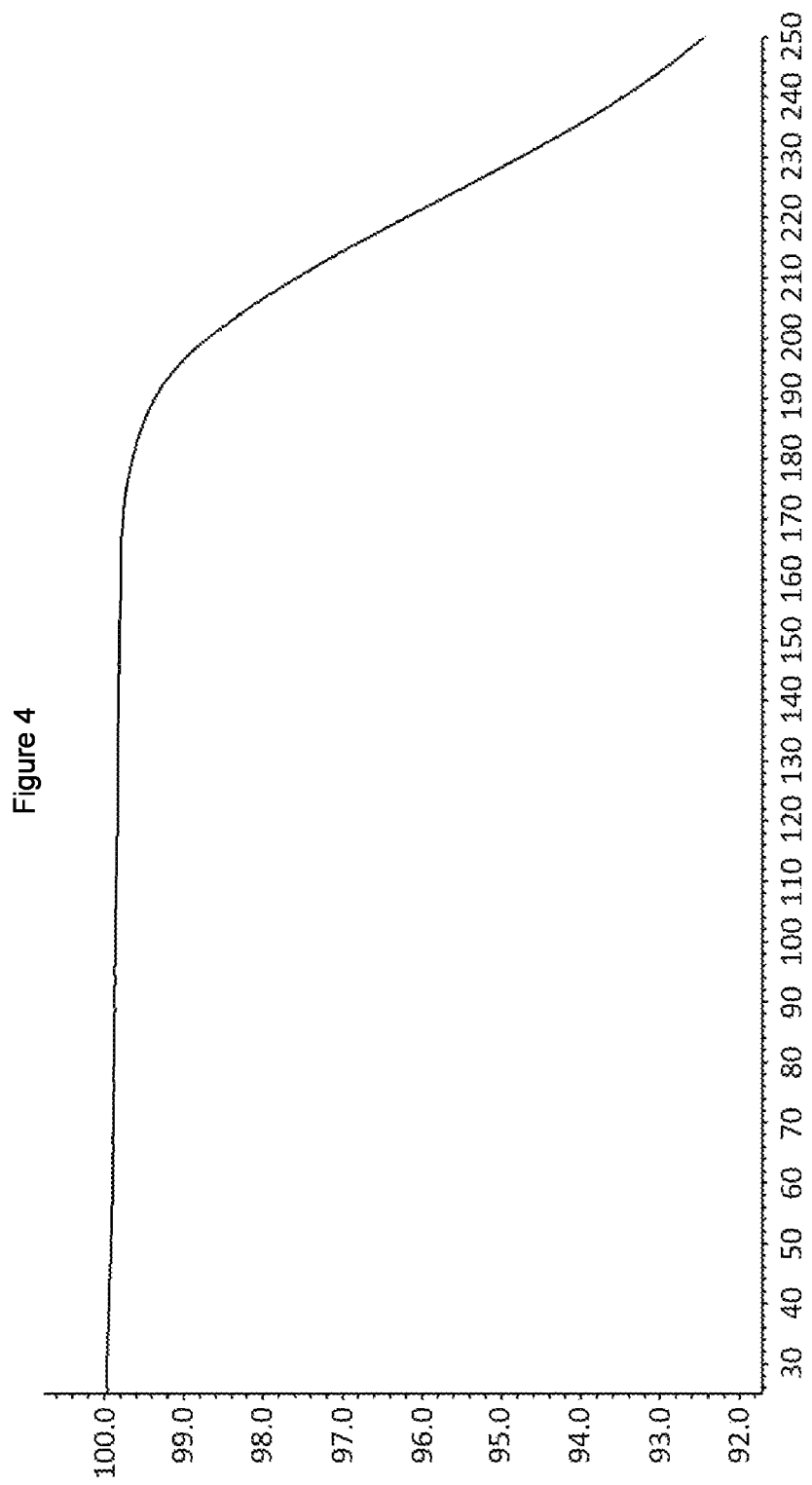
FIG. 4: illustrates a representative TGA curve of vadadustat L-proline Form 1 according to the present invention. The x-axis shows the temperature in degree Celsius (° C.), the y-axis shows the mass (loss) of the sample in weight percent (weight %).

The TGA curve of vadadustat L-proline form 1 of the present invention, which is displayed in FIG. 4 herein, shows no significant mass loss until the sample melts. For example, a mass loss only about 0.20 weight % was observed up to a temperature of about 170° C., which is a strong indication for the presence of an anhydrous and non-solvated crystal form.

Example 2: Preparation of Vadadustat L-Proline Form 2

A suspension of Vadadustat (152 mg, 496 mmol, e.g. prepared according to the procedure disclosed in Example 4 of WO 2012/170377 A1) and L-proline (69 mg, 504 mmol) 2-propanol was stirred at RT for 18 hours. The solid was collected by filtration and dried for 24 hours at room temperature under vacuum (~10 mbar) to obtain vadadustat L-proline form 2.

Yield: 159 mg

Powder X-Ray Diffraction

A representative diffractogram of vadadustat L-proline form 2 according to the present invention is displayed in FIG. 5 and the corresponding reflection list (peak list) from 2 to 30° 2-Theta is provided in table 3 below.

TABLE 3

Reflection (peak) positions of vadadustat L-proline form 2
according to the present invention in the range of from 2 to 30°
2-Theta; A typical precision of the 2-Theta values is in the range
of ±0.2° 2-Theta, preferably of ±0.1° 2-Theta.

| Reflection position [° 2-Theta] |
|---|
| 5.2 |
| 6.4 |
| 6.8 |
| 8.4 |
| 10.2 |
| 10.5 |
| 10.8 |
| 11.4 |
| 12.9 |
| 15.7 |
| 16.2 |
| 16.9 |
| 17.3 |
| 18.1 |
| 19.3 |
| 19.6 |
| 20.2 |
| 20.5 |
| 20.9 |
| 21.1 |
| 21.9 |
| 22.4 |
| 23.3 |
| 24.0 |
| 24.7 |
| 25.1 |
| 26.1 |
| 26.6 |
| 27.2 |
| 27.9 |
| 29.4 |

Fourier Transform Infrared Spectroscopy

A representative FTIR spectrum of vadadustat L-proline form 2 according to the present invention is displayed in FIG. 6 and the corresponding peak list is provided in table 4 below.

TABLE 4

FTIR peak list of vadadustat L-proline according to the present invention; a typical precision of the wavenumbers is in the range of ±4 cm$^{-1}$, preferably of ±2 cm$^{-1}$.

| Wavenumber [cm$^{-1}$] |
| --- |
| 3383 |
| 3130 |
| 1718 |
| 1649 |
| 1585 |
| 1561 |
| 1530 |
| 1461 |
| 1437 |
| 1384 |
| 1325 |
| 1285 |
| 1215 |
| 1192 |
| 1084 |
| 1042 |
| 998 |
| 954 |
| 929 |
| 876 |
| 842 |
| 784 |
| 760 |
| 687 |
| 638 |

Differential Scanning Calorimetry

Figure 7:
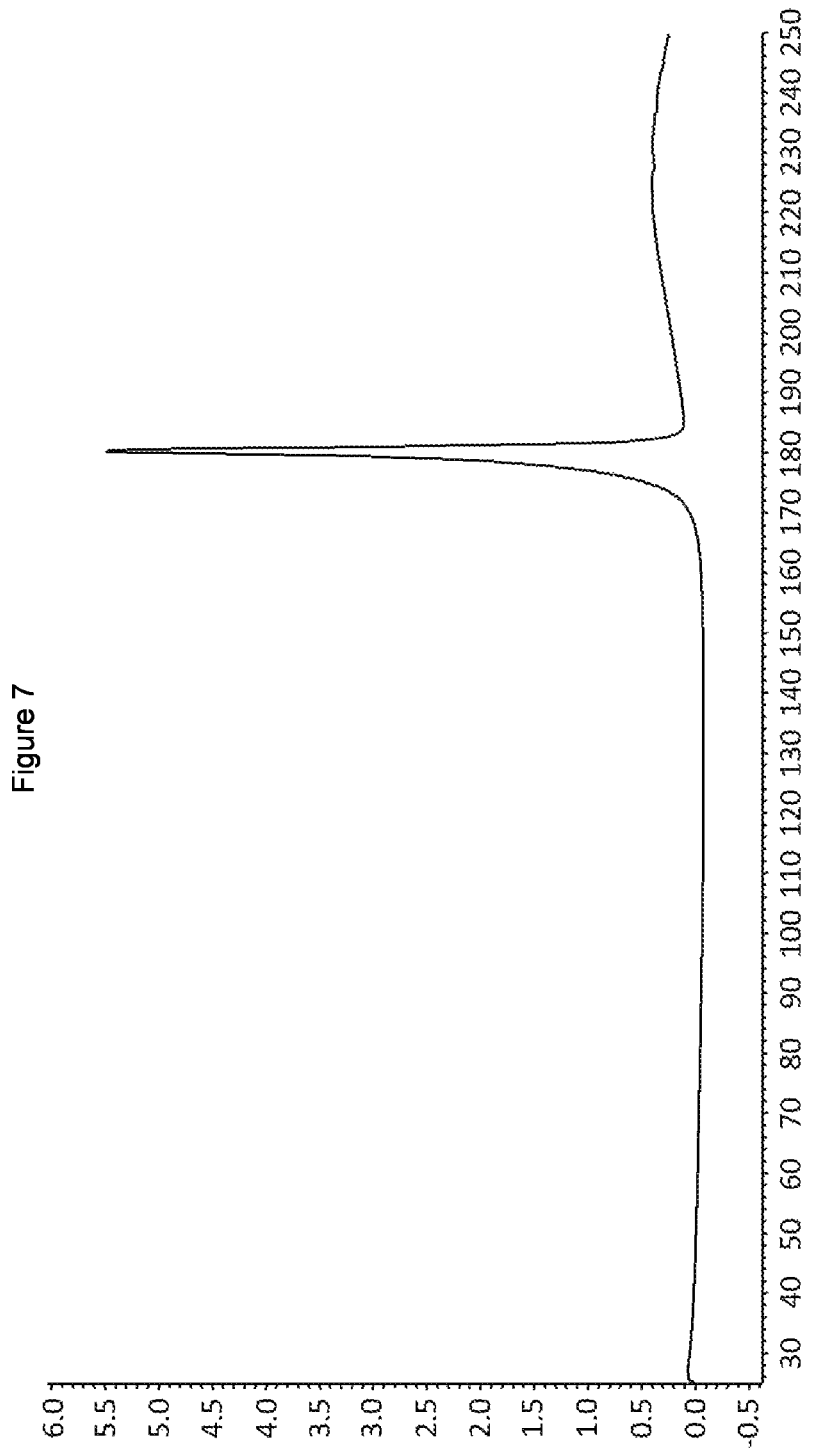
FIG. 7: illustrates a representative DSC curve of vadadustat L-proline Form 2 according to the present invention. The x-axis shows the temperature in degree Celsius (° C.), the y-axis shows the heat flow rate in Watt per gram (W/g) with endothermic peaks going up.

The DSC curve of vadadustat L-proline form 2 of the present invention, which is displayed in FIG. 7 herein, shows a single endothermic peak with an onset at a temperature of about 178° C., a peak at a temperature of about 179° C., and an enthalpy of about 90 J/g, which is due to the melting of the crystalline form. No other thermal events are visible until the crystalline form melts, indicating that vadadustat L-proline form 2 of the present invention undergoes no phase transformations but is stable until it melts.

Thermogravimetric Analysis

Figure 8:
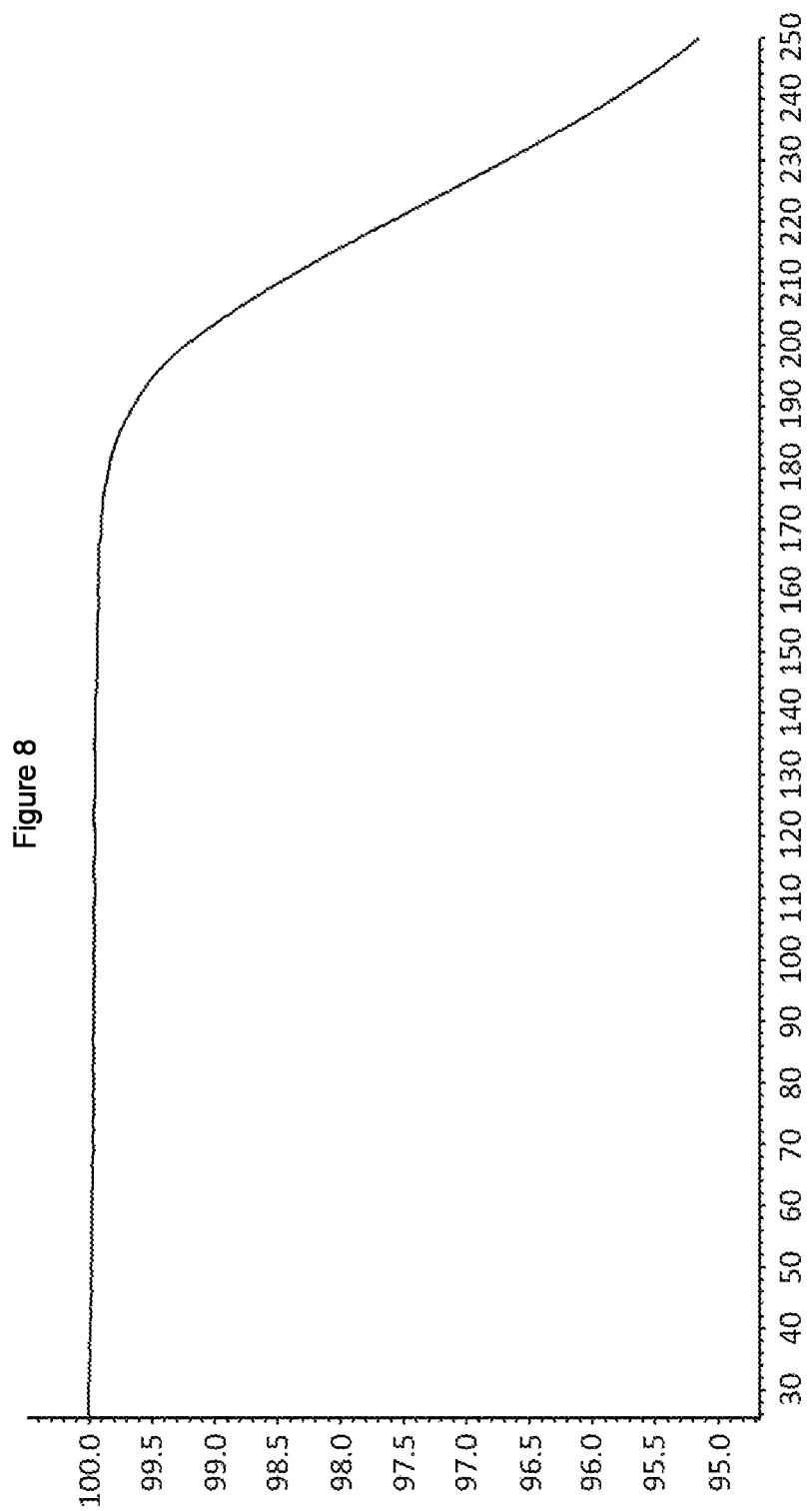
FIG. 8: illustrates a representative TGA curve of vadadustat L-proline Form 2 according to the present invention. The x-axis shows the temperature in degree Celsius (° C.), the y-axis shows the mass (loss) of the sample in weight percent (weight %).

The TGA curve of vadadustat L-proline form 2 of the present invention, which is displayed in FIG. 8 herein, shows no significant mass loss until the sample melts. For example, a mass loss only about 0.15 weight % was observed up to a temperature of about 180° C., which is a strong indication for the presence of an anhydrous and non-solvated crystal form.

Example 3: Alternative Preparation of Vadadustat L-Proline Form 1

Vadadustat (122 mg, 398 mmol, e.g. prepared according to the procedure disclosed in Example 4 of WO 2012/170377 A1) and L-proline (69 mg, 599 mmol) were dissolved in a mixture of methanol (1 mL) and THF (1 mL) upon slight heating. The obtained clear solution was stirred at RT for 2.5 hours, whereat crystallization occurred. The solid was collected by filtration and dried for 18 hours at room temperature under vacuum (~10 mbar) to obtain vadadustat L-proline form 1.

Yield: 63 mg

Example 4: Alternative Preparation of Vadadustat L-Proline Form 2

Vadadustat (149 mg, 486 mmol, e.g. prepared according to the procedure disclosed in Example 4 of WO 2012/170377 A1) and L-proline (56 mg, 486 mmol) were dissolved in methanol (4 mL) upon slight heating. The obtained clear solution was stirred at RT for 2 hours, whereat crystallization occurred. The solid was collected by filtration and dried for 18 hours at room temperature under vacuum (~10 mbar) to obtain vadadustat L-proline form 2.

Example 5: Film-Coated Tablets Comprising Crystalline Vadadustat L-Proline

| Formulation 1 | | |
| --- | --- | --- |
| | mg/tablet | |
| Ingredient | intragranular | extragranular |
| Vadadustat L-proline form 1 | 228.83* | |
| Microcrystalline cellulose | 57.46 | |
| Sodium starch glycolate | 6.90 | 6.90 |
| Hydroxypropyl methylcellulose | 6.44 | |
| Colloidal silicon dioxide | | 0.575 |
| Magnesium stearate | | 1.725 |

Film coating: 2.0-6.0 weight % of Opadry®
*Equivalent to 150 mg vadadustat

| Formulation 2 | | |
| --- | --- | --- |
| | mg/tablet | |
| Ingredient | intragranular | extragranular |
| Vadadustat L-proline form 2 | 206.31* | |
| Microcrystalline cellulose | 57.46 | |
| Sodium starch glycolate | 6.90 | 6.90 |
| Hydroxypropyl methylcellulose | 6.44 | |
| Colloidal silicon dioxide | | 0.575 |
| Magnesium stearate | | 1.725 |

Film coating: 2.0-6.0 weight % of Opadry®
*Equivalent to 150 mg vadadustat

The manufacturing/packaging procedure for the vadadustat L-proline Form 1 tablets is divided into four unit processes:

1. mixing vadadustat L-proline form 1 with intragranular excipients, roller compaction or slugging, milling, and blending with extragranular excipients to yield the final powder blend for vadadustat L-proline form 1
2. tablet compression to yield tablet cores
3. tablet film-coating to yield film-coated tablets; and
4. packaging Reference Example 1: Preparation of Vadadustat 1,4-Dioxane Solvate Vadadustat (5.1 g, 16.63 mol) was dissolved in 1,4-dioxane (100 mL). The solution was filtered through a 0.45 micrometer Milipore syringe filter. Lyophilization was accomplished using a Christ LSC plus lyophilisator and applying the following program:

| | temperature [° C.] | time [h] | pressure [mbar] |
|---|---|---|---|
| loading | −20 | — | ambient |
| freezing | −20 | 1 | ambient |
| drying | −20 | 2 | ambient --> 0.120 |
| | −20 | 10 | 0.120 |
| | −20 --> −5 | 2 | 0.120 |
| | −5 | 10 | 0.120 |
| | −5 --> 10 | 2 | 0.120 |
| | 10 | 10 | 0.120 |
| | 10 --> 25 | 2 | 0.120 |
| | 25 | 10 | 0.120 |
| post-drying | 25 | 1 | 0.120 --> 0.0010 |
| | 25 | 72 | 0.0010 |

Vadadustat 1,4-dioxane solvate was obtained quantitatively.

Powder X-Ray Diffraction

Figure 9:
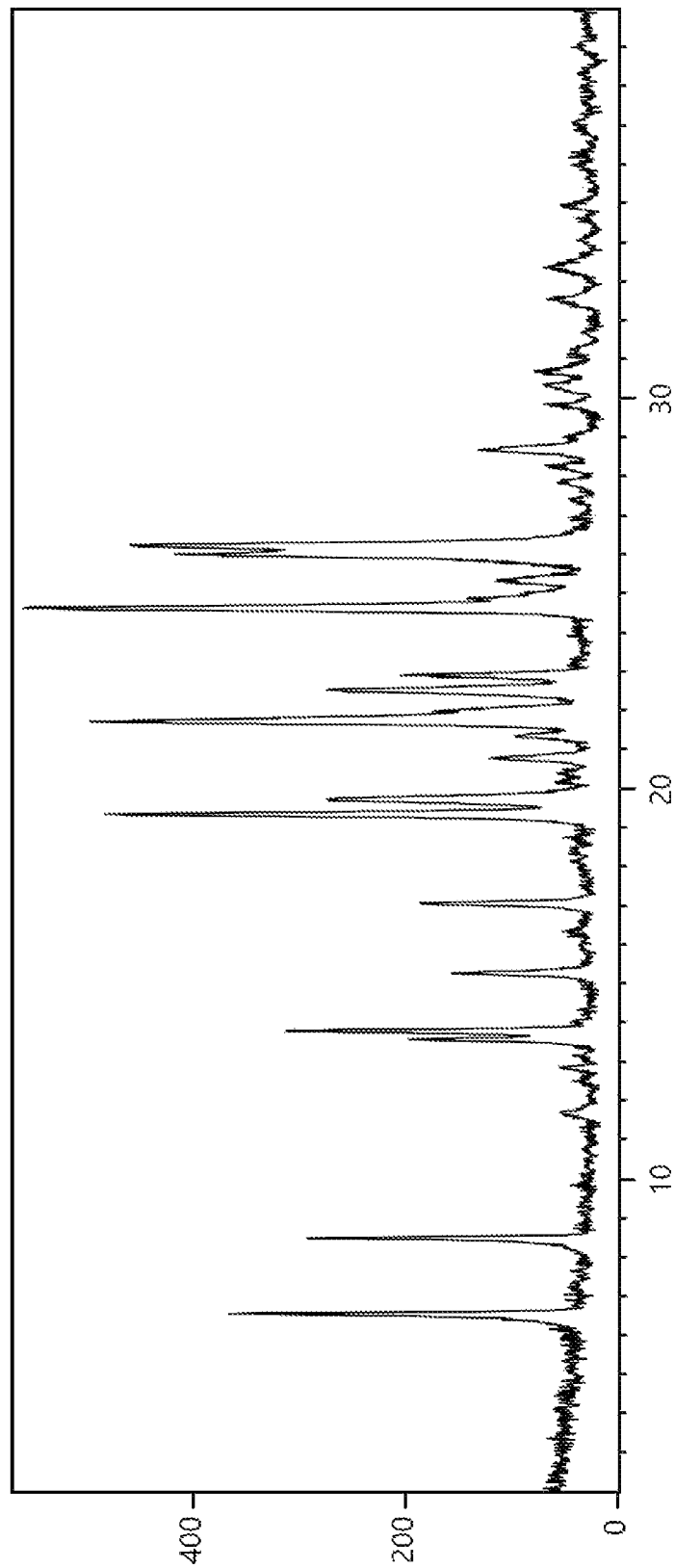
FIG. 9: illustrates a representative PXRD of vadadustat 1,4-dioxane solvate. The x-axis shows the scattering angle in ° 2-Theta, the y-axis shows the intensity of the scattered X-ray beam in counts of detected photons.

A representative diffractogram of vadadustat 1,4-dioxane solvate is displayed in FIG. 9 and the corresponding reflection list (peak list) from 2 to 30° 2-Theta is provided in table 5 below.

TABLE 5

Reflection (peak) positions of vadadustat 1,4-dioxane in the range of from 2 to 30° 2-Theta; A typical precision of the 2-Theta values is in the range of ±0.2° 2-Theta, preferably of ±0.1° 2-Theta.

| Reflection position [° 2-Theta] |
|---|
| 6.6 |
| 8.5 |
| 11.7 |
| 12.9 |
| 13.6 |
| 13.8 |
| 15.3 |
| 17.1 |
| 19.4 |
| 19.7 |
| 20.8 |
| 21.4 |
| 21.7 |
| 22.6 |
| 22.9 |
| 24.7 |
| 25.4 |
| 26.0 |
| 26.3 |
| 27.9 |
| 28.2 |
| 28.7 |
| 29.0 |
| 29.8 |

Fourier Transform Infrared Spectroscopy

Figure 10:
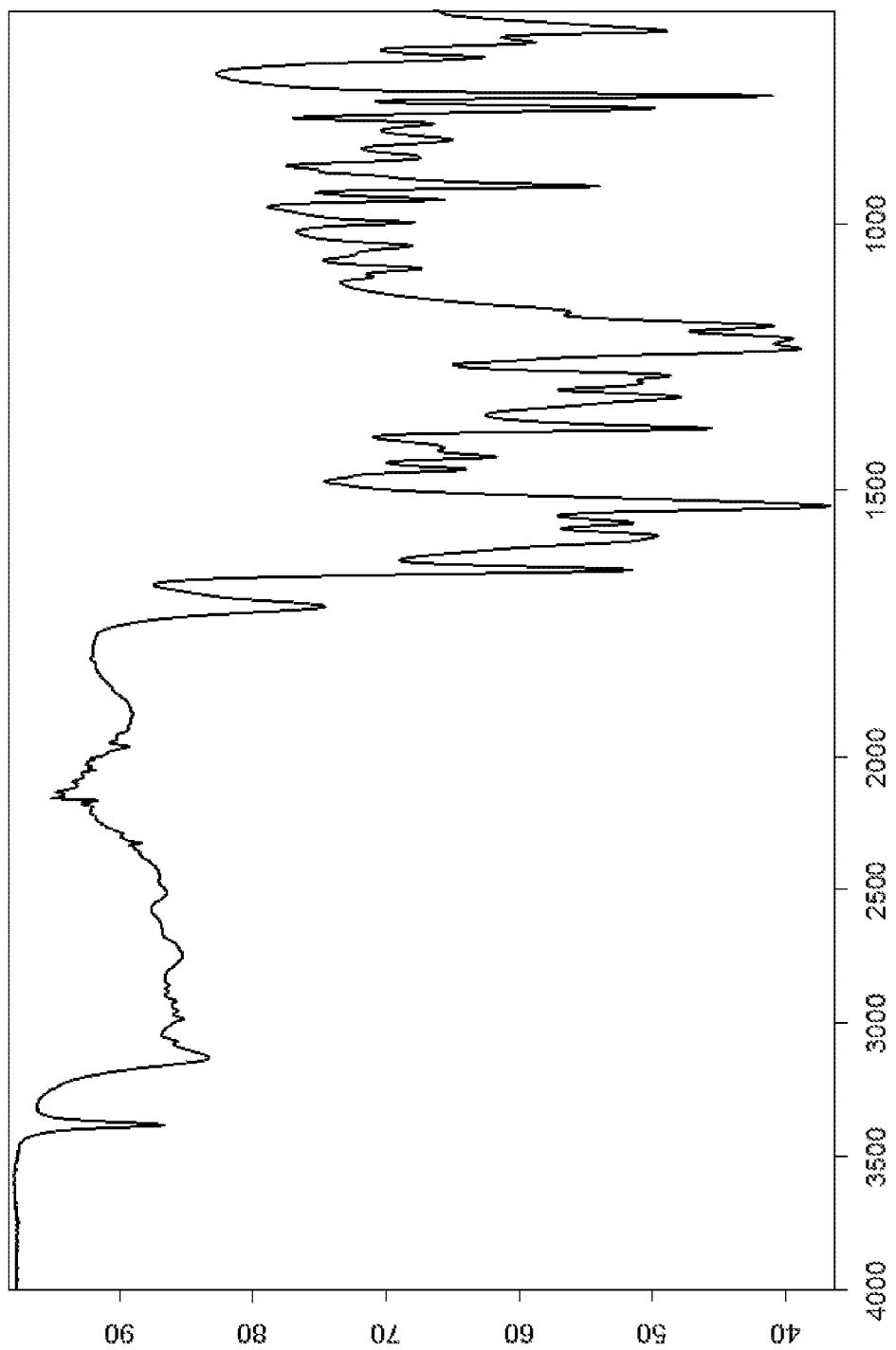
FIG. 10: illustrates a representative FTIR spectrum of vadadustat 1,4-dioxane solvate according to the present invention. The x-axis shows the wavenumbers in $cm^{-1}$, the y-axis shows the relative intensity in percent transmittance.

A representative FTIR spectrum of vadadustat 1,4-dioxane solvate is displayed in FIG. 10 and the corresponding peak list is provided in table 6 below.

TABLE 6

FTIR peak list of vadadustat 1,4-dioxane; a typical precision of the wavenumbers is in the range of ±4 cm$^{-1}$, preferably of ±2 cm$^{-1}$.

| Wavenumber [cm$^{-1}$] |
|---|
| 3389 |
| 2964 |
| 2918 |
| 2863 |
| 1734 |
| 1657 |
| 1584 |
| 1542 |
| 1492 |
| 1458 |
| 1427 |
| 1385 |
| 1346 |
| 1295 |
| 1253 |
| 1237 |
| 1192 |
| 1116 |
| 1076 |
| 1045 |
| 992 |
| 946 |
| 919 |
| 894 |
| 864 |
| 826 |
| 786 |
| 761 |
| 692 |
| 660 |
| 638 |

Differential Scanning Calorimetry

Figure 11:
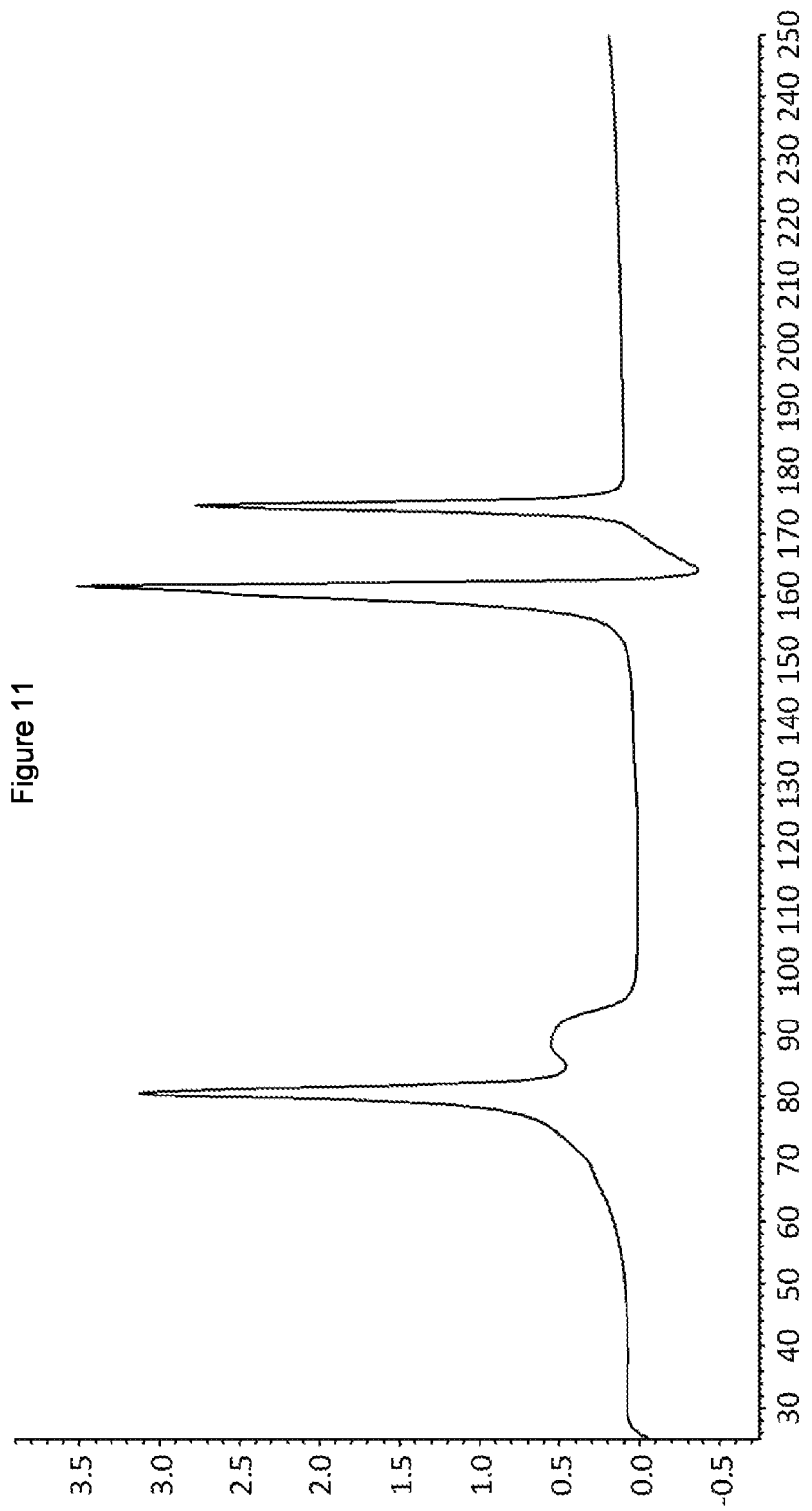
FIG. 11: illustrates a representative DSC curve of vadadustat 1,4-dioxane solvate. The x-axis shows the temperature in degree Celsius (° C.), the y-axis shows the heat flow rate in Watt per gram (W/g) with endothermic peaks going up.

The DSC curve of vadadustat 1,4-dioxane, which is displayed in FIG. 11 herein, shows a first broad endothermic peak with an onset at a temperature of about 78° C., which is caused by the release of 1,4-dioxane from the crystal structure. After desolvation the presence of Form CS1 of WO 2018/108101 A1 was confirmed by PXRD. Form CS1 then melts, which is indicated by a second endotherm having an onset at a temperature of about 158° C. and a peak at about 161° C. Immediately after melting, Form A of WO 2015/073779 A1 crystallizes from the melt, which is indicated by an exothermic signal having an onset at a temperature of about 163° C. and a peak at about 164° C. The presence of Form A has been again confirmed by PXRD. Finally, Form A melts, which is indicated by the endothermic signal having an onset at a temperature of about 173° C. and a peak at about 174° C.

Thermogravimetric Analysis

Figure 12:
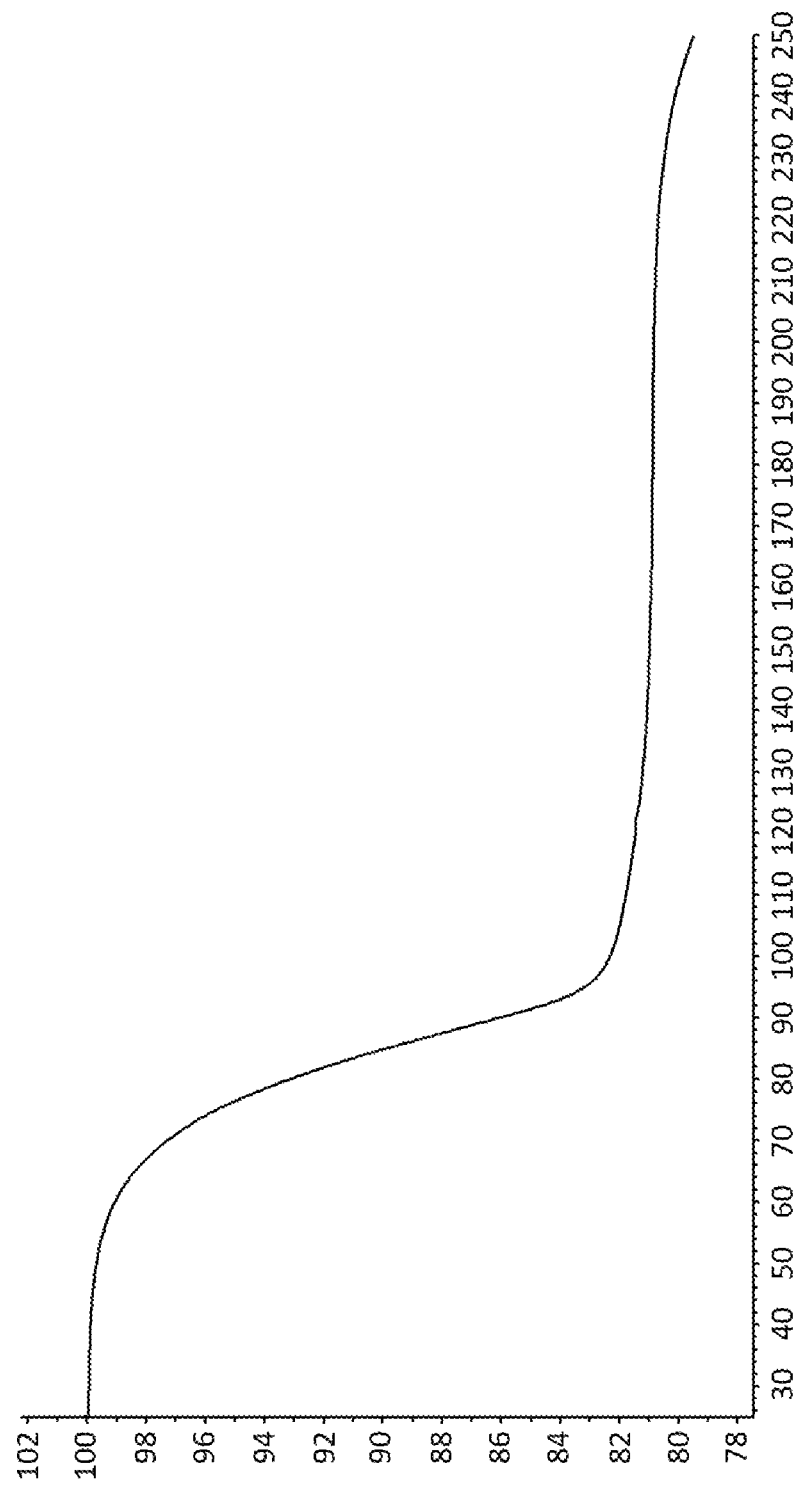
FIG. 12: illustrates a representative TGA curve of vadadustat 1,4-dioxane solvate according to the present invention. The x-axis shows the temperature in degree Celsius (° C.), the y-axis shows the mass (loss) of the sample in weight percent (weight %).

The TGA curve of vadadustat 1,4-dioxane solvate, which is displayed in FIG. 12 herein, shows a massive mass loss of about 19 weight % up to a temperature of about 170° C., wherein the mass loss already starts at a temperature as low as about 40° C.

Comparative Example 1: Thermal Stability of Various Multi-Component Vadadustat Crystals Comparing thermoanalytical data such as DSC and TGA results of the various multi-component crystal forms of vadadustat clearly shows, that Form 1 and Form 2 of the present invention are physically stable toward temperature stress e.g. they show no thermal events in DSC experiments until they start to melt at about 170° C. and 178° C., respectively. Also, no significant mass loss is visible in the TGA curves of Form 1 and Form 2 until they melt.

In contrast, the vadadustat hydrate of WO 2018/108101 A1 as well as the 1,4-dioxane solvate disclosed herein both readily lose their water and organic solvent upon temperature stress. Hence, the thermal stabilities of Form 1 and Form 2 of vadadustat L-proline of the present invention are superior compared to the thermal stability of vadadustat hydrate of WO 2018/108101 A1 and the 1,4-dioxane solvate disclosed herein. A summary of the thermal stabilities of the various multicomponent crystal forms of vadadustat is provided in table 7 below.

TABLE 7

Summary of thermal stability of various multicomponent crystal forms of vadadustat

| Multicomponent Form | Thermal stability |
|---|---|
| Vadadustat L-proline form 1 | physically stable until melting at about 170° C. |
| Vadadustat L-proline form 2 | physically stable until melting at about 178° C. |
| Vadadustat 1,4-dioxane solvate | desolvation below 100° C. |
| Vadadustat hydrate | dehydration below 100° C. |

The invention claimed is:

1. A crystalline compound consisting essentially of a co-crystal of vadadustat and L-proline.

2. The compound of claim 1 characterized by the chemical structure according to Formula (II)

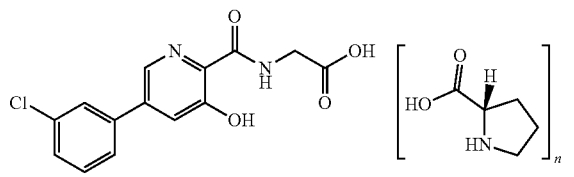

Formula (II)

Formula (II)
wherein n is in the range of from 0.7 to 1.7.

3. A crystalline compound according to claim 1, defined as Form 1, characterized by having a powder X-ray diffractogram comprising reflections at 2-Theta angles of (8.2±0.2)°, (18.8±0.2)° and (25.2±0.2)°, when measured at a temperature in the range of from 20 to 30° C. with Cu-Kalpha$_{1,2}$ radiation having a wavelength of 0.15419 nm.

4. The crystalline compound of claim 3, characterized by having a Fourier transform infrared spectrum comprising peaks at wavenumbers of (3378±4) cm$^{-1}$, (3217±4) cm$^{-1}$ and (1651±4) cm$^{-1}$, when measured at a temperature in the range of from 20 to 30° C. with a diamond attenuated total reflection cell.

5. The crystalline compound of claim 3, characterized by having a melting point onset at a temperature in the range of from (170±2)° C., when measured with differential scanning calorimetry at a heating rate of 10 K/min.

6. A crystalline compound according to claim 1, defined as Form 2, characterized by having a powder X-ray diffractogram comprising reflections at 2-Theta angles of (8.4±0.2)°, (15.7±0.2)° and (16.2±0.2)°, when measured at a temperature in the range of from 20 to 30° C. with Cu-Kalpha$_{1,2}$ radiation having a wavelength of 0.15419 nm.

7. The crystalline compound of claim 6, characterized by having a Fourier transform infrared spectrum comprising peaks at wavenumbers of (3383±4) cm$^{-1}$, (3130±4) cm$^{-1}$ and (1718±4) cm$^{-1}$, when measured at a temperature in the range of from 20 to 30° C. with a diamond attenuated total reflection cell.

8. The crystalline compound of claim 6, characterized by having a melting point onset at a temperature in the range of from (178±2)° C., when measured with differential scanning calorimetry at a heating rate of 10 K/min.

9. A composition comprising a crystalline compound as defined in claim 1, characterized in that the composition is substantially free of a compound of Formula (III)

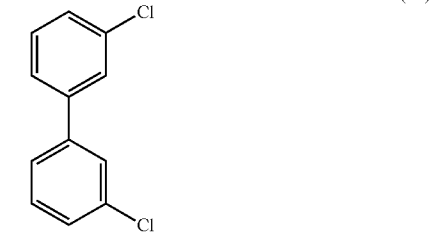

Formula (III)

as determined by GC/MS.

10. A method of preparing a pharmaceutical composition of vadadustat, comprising:
providing a crystalline compound as defined in claim 1, and
mixing said crystalline compound or said composition with at least one pharmaceutically acceptable excipient suitable for preparing the pharmaceutical composition.

11. A pharmaceutical composition comprising a crystalline compound as defined in claim 1 and at least one pharmaceutically acceptable excipient.

12. The pharmaceutical composition according to claim 11, wherein the pharmaceutical composition is an oral solid dosage form.

13. The pharmaceutical composition according to claim 11, wherein the crystalline compound is characterized by having a powder X-ray diffractogram comprising reflections at 2-Theta angles of (8.2±0.2)°, (18.8±0.2)° and (25.2±0.2)°, when measured at a temperature in the range of from 20 to 30° C. with Cu-Kalpha$_{1,2}$ radiation having a wavelength of 0.15419 nm.

14. The pharmaceutical composition according to claim 11, wherein the crystalline compound is characterized by having a powder X-ray diffractogram comprising reflections at 2-Theta angles of (8.4±0.2)°, (15.7±0.2)° and (16.2±0.2)°, when measured at a temperature in the range of from 20 to 30° C. with Cu-Kalpha$_{1,2}$ radiation having a wavelength of 0.15419 nm.

15. A method of treatment of a disease in a patient, comprising administrating to the patient in need of such treatment a crystalline compound as defined in claim 1, wherein the disease is anemia, end-stage renal disease (ESRD), and/or chronic kidney disease (CKD).

16. The method according to claim 15, wherein the disease is anemia.

17. The method according to claim 15, wherein said patient has end-stage renal disease (ESRD) and/or chronic kidney disease (CKD).

* * * * *